United States Patent [19]
Bass et al.

[11] Patent Number: 5,304,472
[45] Date of Patent: Apr. 19, 1994

[54] METHOD OF CONTROLLING POLYPEPTIDE PRODUCTION IN BACTERIAL CELLS

[75] Inventors: Steven Bass, Redwood City; James R. Swartz, Menlo Park, both of Calif.

[73] Assignee: Genentech, Inc., S. San Francisco, Calif.

[21] Appl. No.: 989,845

[22] Filed: Nov. 20, 1992

[51] Int. Cl.$^5$ .................. C12N 1/00; C12N 15/08; C12N 15/31; C12N 15/67

[52] U.S. Cl. .................. 435/69.1; 435/172.3; 435/252.3; 435/252.33; 435/320.1; 935/39; 935/40; 935/10; 935/61; 935/72; 935/73; 536/23.7

[58] Field of Search .................. 435/69.1, 252.33

[56] References Cited

U.S. PATENT DOCUMENTS 4,703,005 10/1987 Nakata et al. .................. 435/69.1

FOREIGN PATENT DOCUMENTS 0441252 8/1991 European Pat. Off. .
2599380 12/1987 France .
6071413 7/1980 Israel .
61-280292 12/1986 Japan .
WO8604089 7/1986 PCT Int'l Appl. .

OTHER PUBLICATIONS

Nakata, A., et al., in Phosphate Metabolism and Cellular Regulation in Microorganisms, Torriani-Gorini et al., Eds., American Society for Microbiology, Washington, D.C., 1987, pp. 150–155.
Luécke, H., et al., Nature, vol. 347, pp. 402–406, Sep. 27, 1990.
Surin, B. P., et al., Journal of Bacteriology, vol. 157, pp. 772–778, Mar. 1984.
Torriani, A., Bioessays, vol. 12, pp. 371–376, 1990.
Worobec, E. A., et al., FEMS Microbiology Letters, vol. 52, pp. 235–238, 1988.
Wanner, J. Cell. Biochem., 51:47–54, (1993), "Gene Regulation by Phosphate in Enteric Bacteria".
Rao et al., J. Bacteriol., 175:74–79, (1993), "Effect of glpT and glpD Mutations on Expression of the phoA Gene in *Escherichia coli*".
Foglino et al., Mol. Gen. Genet., 210:523–527, (1987), "Deletion Analysis of the Promoter Region of the *Escherichia coli* pepN gene, a Gene Subject In Vivo to Multiple Global Controls".
Gharbi et al., J. Bacteriol., 163:1191–1195, (1985), "Multiple Controls Exerted on In Vivo Expression of the pepN gene in *Escherichia coli*: Studies with pepN-lacZ Operon and Protein Fusion strains".
Cooper, Ann. Rev. Microbiol., 38:49–68, (1984), "Metabolism of Methylglyoxal in Microorganisms".
Stock et al., Microbiol. Rev., 53:450–490, (1989), "Protein Phosphorylation and Regulation of Adaptive Response in Bacteria".
Lueke & Quiocho, Nature, "High Specificity of a Phosphate Transport Protein Determined by Hydrogen Bonds", 347:402–406 (1990).

(List continued on next page.)

Primary Examiner—Robert A. Wax
Assistant Examiner—William W. Moore
Attorney, Agent, or Firm—Janet E. Hasak

[57] ABSTRACT

Nucleic acid is provided encoding a molecule having certain variations within the phosphate-binding region of native *E. coli* PstS. Additionally provided are bacterial cells comprising this nucleic acid under control of the native pstS gene promoter, and optionally further comprising nucleic acid encoding a polypeptide of interest under control of the alkaline phosphatase (AP) promoter. Bacterial cells containing both pstS variant nucleic acid and polypeptide nucleic acid are cultured in a medium at a concentration of inorganic phosphate that at all phases of cell growth is above the level at which the cells are starved for phosphate. Alternatively, the cells are cultured under conditions whereby the concentration of inorganic phosphate in the culture medium is controlled during the production period so that the polypeptide is produced under the control of the partially induced AP promoter.

20 Claims, 31 Drawing Sheets

OTHER PUBLICATIONS

Torriani, Biochim. Biophys. Acta, "Influence of Inorganic Phosphate in the Formation of Phosphatases by *Escherichia coli*", 38:460–469 (1960).

Ohinagawa et al., "Structure and Function of the Regulatory Genes for the Phosphate Reguion in *Escherichia coli*", in Phosphate Metabolism and Cellular Regulation in Microorganisms, Torriani-Gorini, eds., American Society for Microbiology, Washington, D.C., 1987, pp. 20–25.

Wanner, "Phosphate Regulation of Gene Expression in *Escherichia coli*", in Neidharat et al., ed., *Escherichia coli* and *Salmonella typhimurium*: Cellular and Molecular Biology, American Society for Microbiology, Washington, D.C., 1987, pp. 1326–1333.

Torriani, "From Cell Membrane to Nucleotides: The Phosphate Regulon in *Escherichia coli*", Bioessays, 12(8):371–376 (1990).

Matin et al., "Genetic Basis of Starvation Survival in Nondifferentiating Bacteria", Ann. Rev. Microbiol., 43:293–316 (1989).

Iwakura et al., "Isolation of DNA Fragment Containing phoS Gene of *Escherichia coli* K–12", J. Biochem., 92:615–622 (1982).

Nagota et al., "Nucleotide Sequence of the phoS Gene, the Structural Gene for the Phosphate-Binding Protein of *Escherichia coli*", J. Bacteriol., 157(3):909–917 (1984).

Surin et al., "Structural Gene for the Phosphate-Repressible Phosphate-Binding Protein of *Escherichia coli* Has Its Own Promoter . . . ", J. Bacteriol., 157(3):772–778 (1984).

Kimura et al., "Regulation of the Phosphate Regulon of *Escherichia coli* . . . ", Mol. Gen. Genet., 215:374–380 (1989).

Levitz et al., "The Effect of the Locus pstB on Phosphate Binding in the Phosphate Specific Transport System of *Escherichi coli*", Mol. Gen. Genet., 200:118–122 (1985).

St. John & Goldberg, "Effects of Starvation for Potassium and Other Inorganic Ions of Protein Degradation and Ribonucleic Acid Synthesis in *Eschericia coli*", 143(3):1223–1233 (1980).

Nakata et al., "Genetic and Biochemical Analysis of the Phosphate-Specific Transport System in *Escherichia coli*", in Phosphate Metabolism and Cellular Regulation in Microorganisms, Torriani Gorini et al., eds., American Society for Microbiology, Washington, D.C. 1987, pp. 150–155.

FIG.1A

```
1    TTCTGTCATC TCTTCGTTAT TAATGTTTGT AATTGACTGA ATATCAACGC TTATTTAAAT
     AAGACAGTAG AGAAGCAATA ATTACAAACA TTAACTGACT TATAGTTGCG AATAAATTTA

61   CAGACTGAAG ACTTTATCTC TCTGTCATAA AACTGTCATA TTCCTTACAT ATAACTGTCA
     GTCTGACTTC TGAAATAGAG AGACAGTATT TTGACAGTAT AAGGAATGTA TATTGACAGT

121  CCTGTTTGTC CTATTTTGCT TCTCGTAGCC AACAAACAAT GCTTTATGAA TCCTCCCAGG
     GGACAAACAG GATAAAACGA AGAGCATCGG TTGTTTGTTA CGAAATACTT AGGAGGGTCC

181  AGACATT ATG AAA GTT ATG CGT ACC ACC GTC GCA ACT GTT GTC GCC GCG
             ATG TAC TTT CAA GCA TGG CAG CGT TGA CAA CAG CGG CGC
             Met Lys Val Met Arg Thr Thr Val Ala Thr Val Val Ala Ala
     -25

230  ACC TTA TCG ATG AGT GCT TTC TCT GTG TTT GCA GAA GCA AGC CTG ACA
     TGG AAT AGC TAC TCA CGA AAG CAC AAA CGT CTT CGT TCG GAC TGT
     Thr Leu Ser Met Ser Ala Phe Ser Val Phe Ala Glu Ala Ser Leu Thr
     -11

278  GGT GCA GGT GCA ACC TTC CCT GCG CCG GGC TAT GCC AAA TGG GCT GAC
     CCA CGT CCA CGT TGG AAG GGA CGC CAC ATA CGG TTT ACC CGA CTG
     Gly Ala Gly Ala Thr Phe Pro Ala Pro Val Tyr Ala Lys Trp Ala Asp
     6
```

FIG. 1B

```
326 ACT TAC CAG AAA GAA ACC GGT AAT AAA GTT AAC TAC CAG GGT ATC GGT
    TGA ATG GTC TTT CTT TGG CCA TTA TTT CAA TTG ATG GTC CCA TAG CCA
 22 Thr Tyr Gln Lys Glu Thr Gly Asn Lys Val Asn Tyr Gln Gly Ile Gly

374 TCT TCC GGT GGC GTA AAA CAG ATT ATC GCT AAT GTT GAT TTT GGT
    AGA AGG CCA CCA CAT TTT GTC TAA TAG CGA TTA CAA CTA AAA CCA
 38 Ser Ser Gly Gly Val Lys Gln Ile Ile Ala Asn Val Asp Phe Gly

422 GCC TCT GAC GCG CCG CTG TCT GAC GAA AAA CTG GCT CAG GAA GGT CTG
    CGG AGA CTG CGC GGC GAC AGA CTG CTT TTT GAC CGA GTC CTT CCA GAC
 54 Ala Ser Asp Ala Pro Leu Ser Asp Glu Lys Leu Ala Gln Glu Gly Leu

470 TTC CAG TTC CCG ACC GTG ATT GGC GAA CTG GTG CTG GCG GTT AAC ATT
    AAG GTC AAG GGC TGG CAC TAA CCG CTT GAC CAC CGC CAA TTG TAA
 70 Phe Gln Phe Pro Thr Val Ile Gly Glu Leu Val Val Leu Ala Asn Ile

518 CCA GGG CTG AAG TCT GGC GAA CTG GAT GGT AAA ACC CTC GGC
    GGT CCC GAC TTC AGA CCG CTT GAC CTA CCA TTT TGG GAG CCG
 86 Pro Gly Leu Lys Ser Gly Glu Leu Asp Gly Lys Thr Leu Gly

566 GAC ATC TAC CTG GGC AAA ATC AAG TGG GAT GAT GAA GCC ATC GCC
    CTG TAG ATG GAC CCG TTT TAG TTC ACC CTA CTA CTT CGG TAG CGG
102 Asp Ile Tyr Leu Gly Lys Ile Lys Lys Trp Asp Asp Glu Ala Ile Ala
```

FIG. 1C

```
614 AAA CTG AAT CCG GGT CTG AAA CTG CCT TCA CAA AAC ATT GCT GTA GTA
    TTT GAC TTA GGC CCA GAC TTT GAC GGA AGT GTT TTG TAA CGA CAT CAT
118 Lys Leu Asn Pro Gly Leu Lys Leu Pro Ser Gln Asn Ile Ala Val Val

662 CGC CGC GCA GAT GGC TCC GGG ACT TCC TTC GTC TTC ACC AGC TAC CTG
    GCG GCG CGT CTA CCG AGG CCC TGA AGG AAG CAG AAG TGG TCG ATG GAC
134 Arg Arg Ala Asp Gly Ser Gly Thr Ser Phe Val Phe Thr Ser Tyr Leu

710 GCG AAA GTG AAC GAA GAG TGG AAA AAC AAC GTT GGT ACT GGC TCT ACC
    CGC TTT CAC TTG CTT CTC ACC TTT TTG TTG CAA CCA TGA CCG AGA TGG
150 Ala Lys Val Asn Glu Glu Trp Lys Asn Asn Val Gly Thr Gly Ser Thr

758 GTA AAA TGG CCG ATC GGT CTG GGC GGT AAA GGT AAC GAC GGT ATC GCC
    CAT TTT ACC GGC TAG CCA GAC CCG CCA TTT CCA TTG CTG CCA TAG CGG
166 Val Lys Trp Pro Ile Gly Leu Gly Gly Lys Gly Asn Asp Gly Ile Ala
```

FIG.1D

```
 806  GCG TTC GTT CAG CGT CTG CCG GGT GCA ATT GGT TAT GTT GAA TAT GCT
      CGC AAG CAA GTC GCA GAC GGC CCA CGT TAA CCA CAA CTT ATA CGA
 182  Ala Phe Val Gln Arg Leu Pro Gly Ala Ile Gly Tyr Val Glu Tyr Ala

854  TAC GCG AAG CAG AAC AAC CTG GCG TAC ACC AAA CTG ATC TCC GCT GAT
      ATG CGC TTC GTC TTG TTG GAC CGC ATG TGG TTT GAC TAG AGG CGA CTA
 198  Tyr Ala Lys Gln Asn Asn Leu Ala Tyr Thr Lys Leu Ile Ser Ala Asp

902  GGT AAA CCG GTT AGT CCG ACC GAA AAC TTC GCT AAT GCA GCA AAA
      CCA TTT GGC CAA TCA GGC TGG CTT TTG AAG CGA TTA CGT CGT TTT
 214  Gly Lys Pro Val Ser Pro Thr Glu Asn Phe Ala Asn Ala Ala Lys

950  GGT GCA GAC TGG AGC AAA ACC TTC GCT CAG GAT CTG ACC AAC CAG AAA
      CCA CGT CTG ACC TCG TTT TGG AAG CGA GTC CTA GAC TGG TTG GTC TTT
 230  Gly Ala Asp Trp Ser Lys Thr Phe Ala Gln Asp Leu Thr Asn Gln Lys

998  GGC GAA GAT GCA TGG CCT ATT ACC TCT ACC ACG TTC ATT CTG ATC CAC
      CCG CTT CTA CGT ACC GGA TAA TGG AGA TGG TGC AAG TAA GAC TAG GTG
 246  Gly Glu Asp Ala Trp Pro Ile Thr Ser Thr Thr Phe Ile Leu Ile His

1046  AAA GAT CAG AAG AAA CCA GAA CAA GGC ACA GAA GTG CTG AAA TTC TTC
      TTT CTA GTC TTC TTT GGT CTT GTT CCG TGT CTT CAC GAC TTT AAG AAG
 262  Lys Asp Gln Lys Lys Pro Glu Gln Gly Thr Glu Val Leu Lys Phe Phe
```

FIG.1E

```
1094  GAC TGG GCG TAC AAA ACC GGG GCT AAA CAG GCG AAC GAC CTG GAT TAC
      CTG ACC CGC ATG TTT TGG CCC CGA TTT GTC CGC TTG CTG GAC CTA ATG
278   Asp Trp Ala Tyr Lys Thr Gly Ala Lys Gln Ala Asn Asp Leu Asp Tyr

1142  GCC AGC CTG CCG GAT AGT GTA GTT GAA CAG GTT CGC GCT GCG TGG AAG
      CGG TCG GAC GGC CTA TCA CAT CAA CTT GTC CAA GCG CGA CGC ACC TTC
294   Ala Ser Leu Pro Asp Ser Val Val Glu Gln Val Arg Ala Ala Trp Lys

1190  ACC AAT ATT AAA GAC AGT AGC GGT AAG CCG CTG TAC TAA TAA AACTCCAGG
      TGG TTA TAA TTT CTG TCA TCG CCA TTC GGC GAC ATG ATT ATT TTGAGGTCC
310   Thr Asn Ile Lys Asp Ser Ser Gly Lys Pro Leu Tyr Oc* Oc*

1241  CCGGGTACGG TGTTTTACGC CGCATCCGGC ATTACAAAAT GACTTTGTAA ACGCGTTTAA
      GGCCCATGCC ACAAAATGCG GCGTAGGCCG TAATGTTTTA CTGAAACATT TGCGCAAATT

1301  CTGAAGAG
      GACTTCTC
```

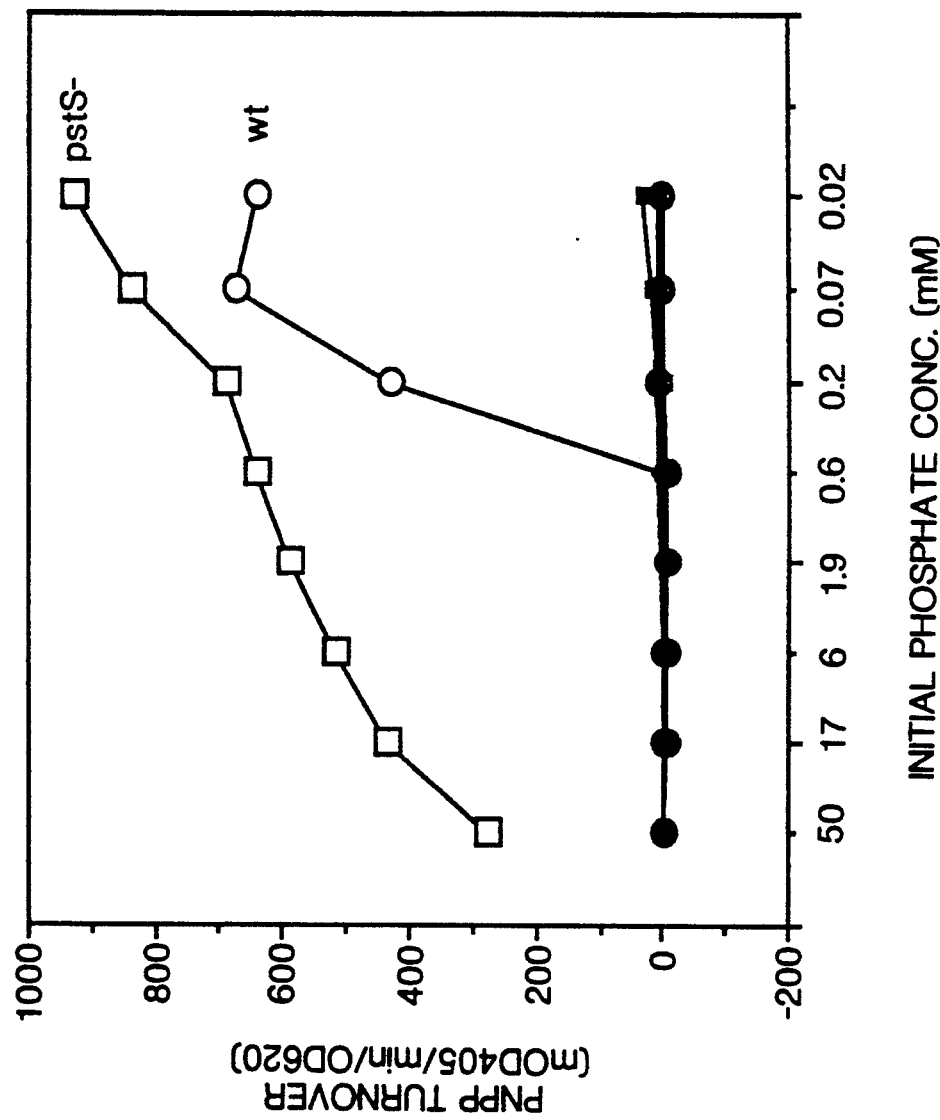

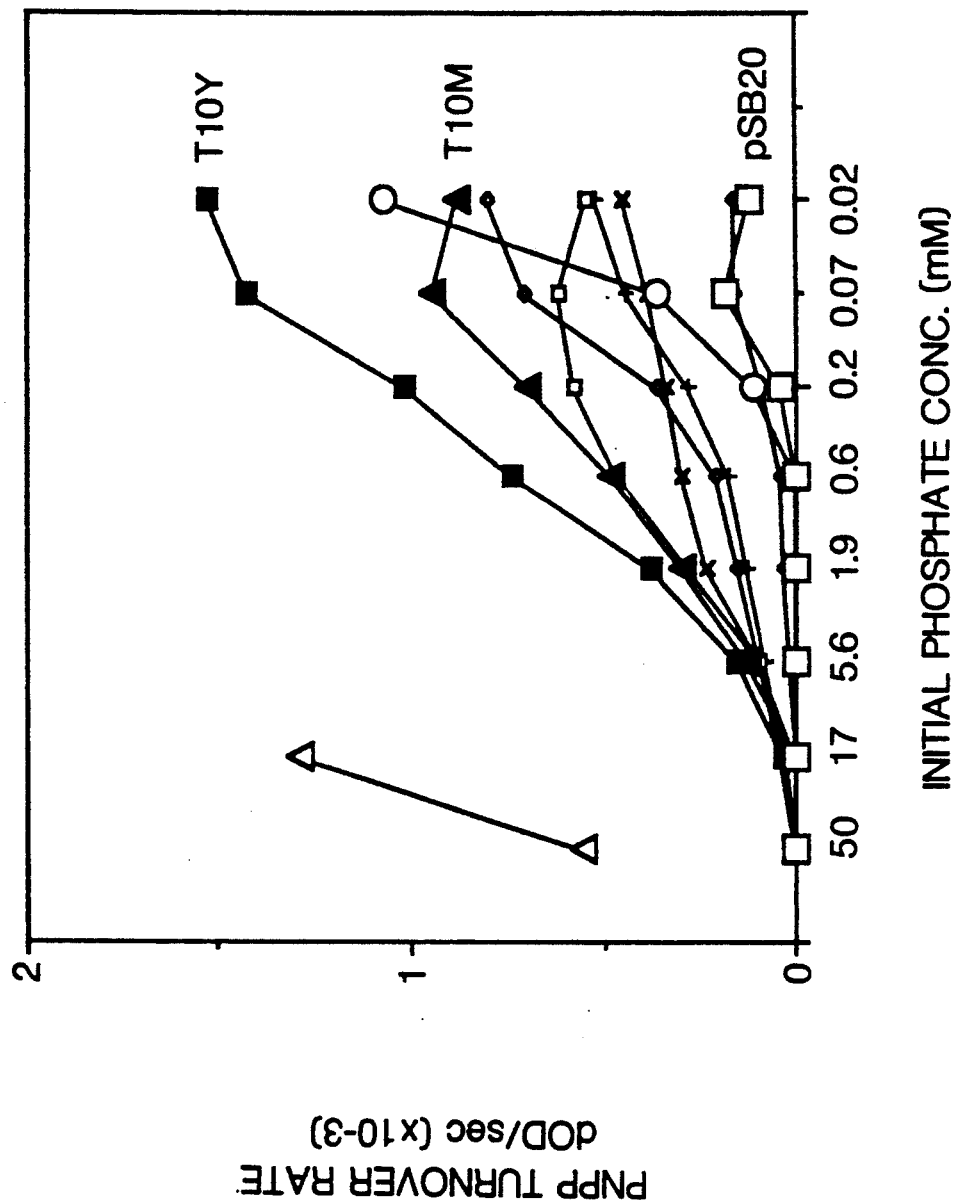

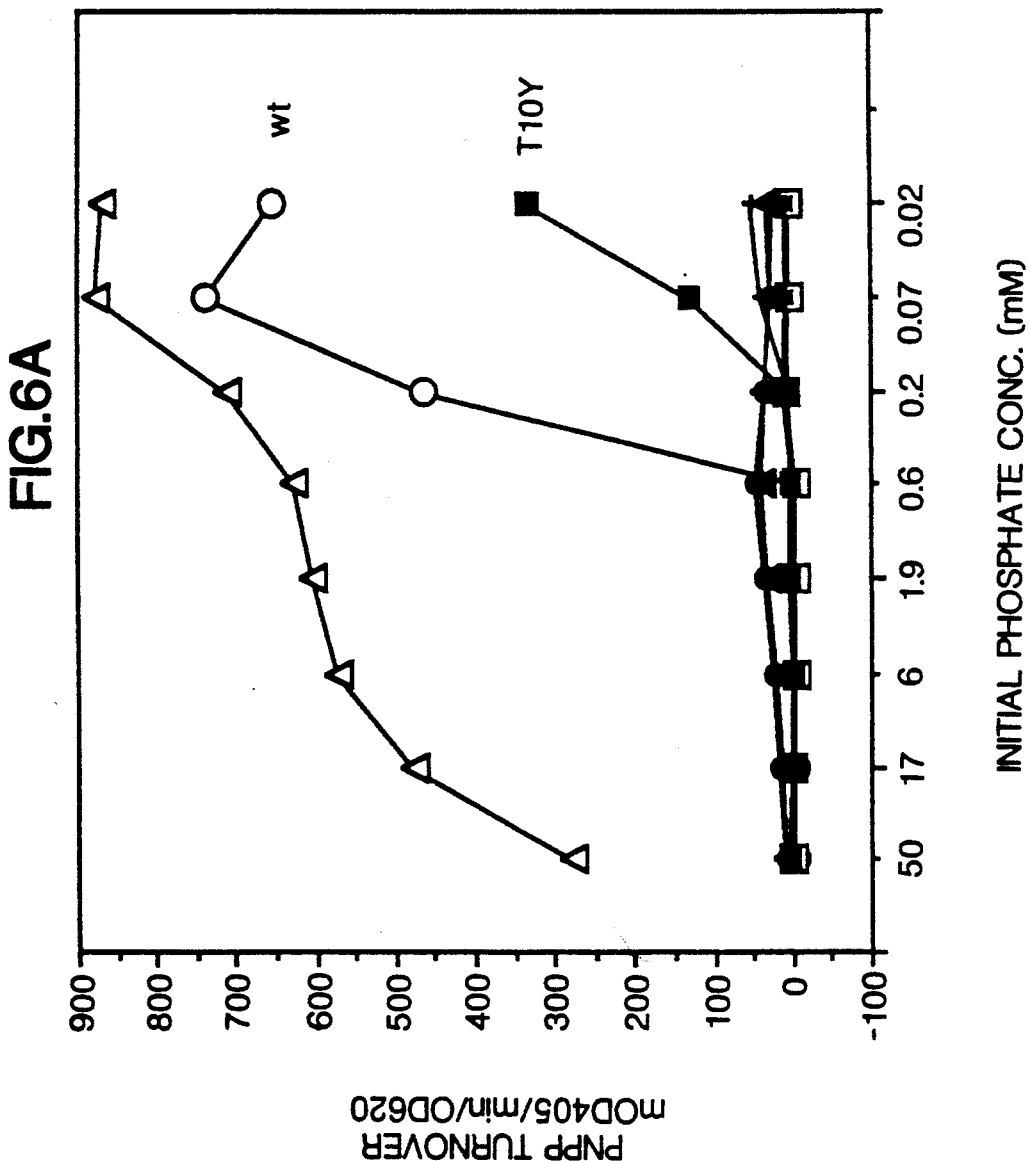

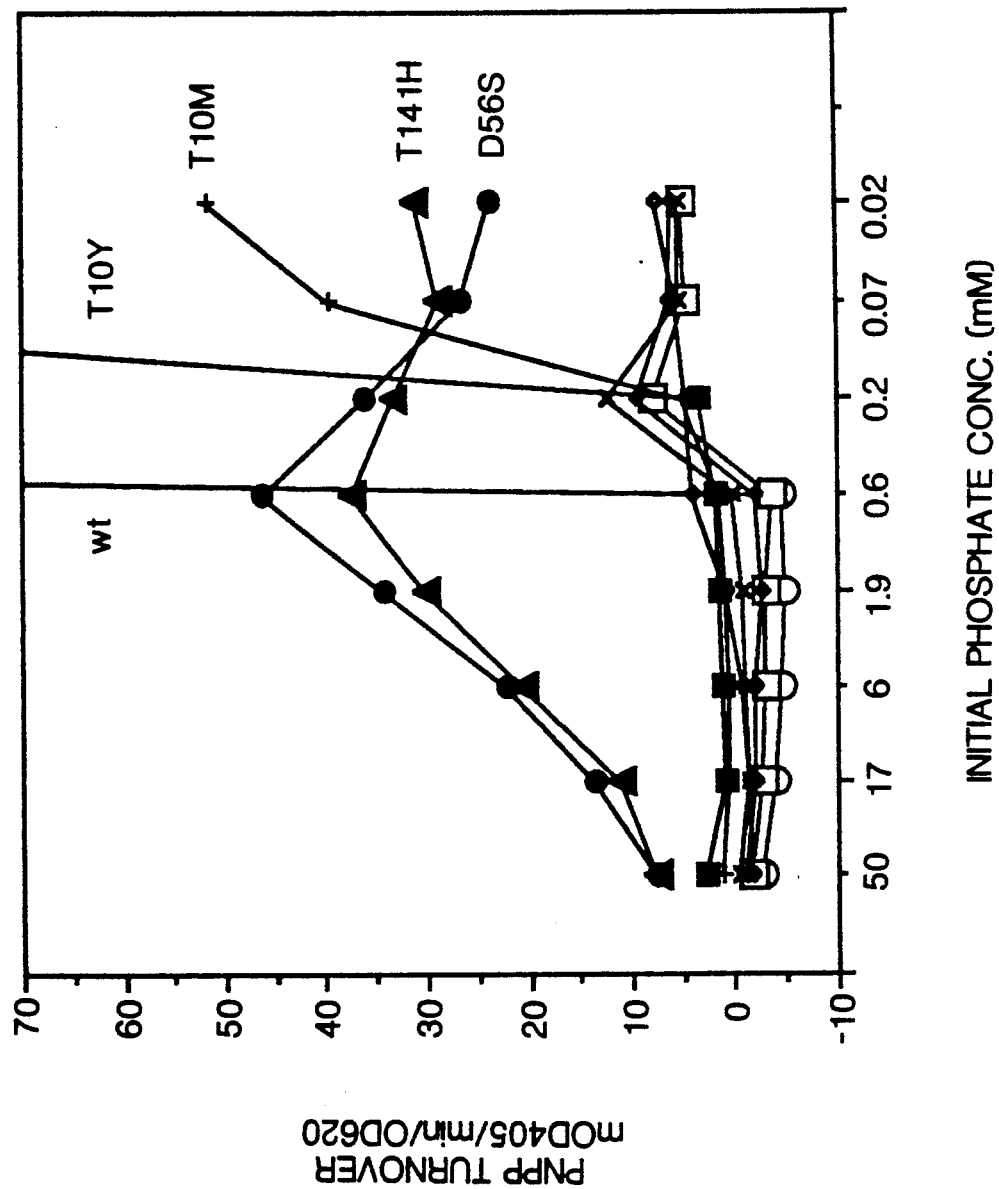

```
GAATTCAACT TCTCCATACT TTGGATAAGG AAATACAGAC ATGAAAAATC  50

TCATTGCTGA GTTGTTATTT AAGCTTGCCC AAAAAGAAGA AGAGTCGAAT 100

GAACTGTGTG CGCAGGTAGA AGCTTTGGAG ATTATCGTCA CTGCAATGCT 150

TCGCAATATG GCGCAAAATG ACCAACAGCG GTTGATTGAT CAGGTAGAGG 200

GGGCGCTGTA CGAGGTAAAG CCCGATGCCA GCATTCCTGA CGACGATACG 250

GAGCTGCTGC GCGATTACGT AAAGAAGTTA TTGAAGCATC CTCGTCAGTA 300

AAAAGTTAAT CTTTTCAACA GCTGTCATAA AGTTGTCACG GCCGAGACTT 350

ATAGTCGCTT TGTTTTTATT TTTAAATGTA TTTGTAACTA GTACGCAAGT 400
```

FIG. 14A

```
TCACGTAAAA AGGGTATCTA GAATTATG  ATG ATT ACT CTG CGC  443
                                Met Ile Thr Leu Arg
                                -24             -20

AAA CTT CCT CTG GCG GTT GCC GTC GCA GCG GGC GTA ATG  482
Lys Leu Pro Leu Ala Val Ala Val Ala Ala Gly Val Met
                                            -10

TCT GCT CAG GCC ATG GCC GGT CCC GAA ACT CTG TGC GGT  521
Ser Ala Gln Ala Met Ala Gly Pro Glu Thr Leu Cys Gly
                        1

GCT GAA CTG GTT GAC GCT CTG CAG TTT GTT TGC GGT GAC  560
Ala Glu Leu Val Asp Ala Leu Gln Phe Val Cys Gly Asp
            10                                  20

CGT GGT TTT TAT AAC AAA CCC ACT GGT TAT GGT TCT  599
Arg Gly Phe Tyr Asn Lys Pro Thr Gly Tyr Gly Ser
                        30
```

FIG. 14B

```
TCT TCT CGT CGT GCT CCC CAG ACT GGT ATT GTT GAC GAA 638
Ser Ser Arg Arg Ala Pro Gln Thr Gly Ile Val Asp Glu
                    40

TGC TGC TTT CGT TCT TGC GAC CTG CGT CGT CTG GAA ATG 677
Cys Cys Phe Arg Ser Cys Asp Leu Arg Arg Leu Glu Met
         50

TAT TGC GCT CCC CTG AAA CCC GCT AAA TCT GCT TAG AAGCTC 719
Tyr Cys Ala Pro Leu Lys Pro Ala Lys Ser Ala AM*
 60                              70

CTAACGCTCGG TTGCCGCCGG GCGTTTTTA TTGTTAA 757

Position Number -24 signifies the start of the lamB signal sequence.
Position NUmber   1 signifies the start of the IGF-I protein.
```

EcoRI (1149)
5'-GAATTCATGAGATTCCTTCAATTTTACTGCAGTTTTATTCGCAGCATCCTCCGCATTAGC

TGCTCCAGTCAACACTACAACAGAAGATGAAACGGCACAAATTCCGGCTGAAGCTGTCATCGGTT

ACTTAGATTTAGAAGGGGATTTCGATGTGCTGTTTGCCATTTTCCAACAGCACAAATAACGGG

TTATTGTTTATAAATACTACTATTGCCAGCATTGCTGCTAAAGAAGAAGGGGTATCTTTGGATAA
                                   HaeII             PstI
AAGAGGTCCGGAAACTCTGTGCGGCTGAGCTGGTTGACGCTCTGCAGTTCGTATGTGGTGATC
                            BamHI
GAGGCTTCTACTTCAACAAACCGACTGGGTACGGATCCTCCTCCTCGTCGTCCGCAAACCGGC

ATCGTTGATGAATGCTGTTTTCGGTCCTGTGACCTTCGCCGTCTGGAAATGTACTGCGCTCCGCT
                        SalI  EcoRI (1633)
GAAACCGGCTAAGTCTGCATAGTCGACGAATTC-3'

METHOD OF CONTROLLING POLYPEPTIDE PRODUCTION IN BACTERIAL CELLS

BACKGROUND OF THE INVENTION

1. Field of the Invention

The present invention is directed to nucleic acid and host cells useful in controlling the production of polypeptides in bacterial host cell cultures. More particularly, the invention relates to nucleic acid encoding PstS variants having mutations in the phosphate-binding region of the native PstS protein that allow regulation of induction of polypeptide synthesis in bacterial cells.

2. Description of Related Art

The pstS (phoS) gene encodes a phosphate-binding periplasmic protein that is part of the high-affinity phosphate transport system mediating phosphate uptake in certain prokaryotic organisms such as *E. coli* with a dissociation constant for phosphate of less than 1 $\mu$M. Medveczky and Rosenberg, *Biochim. Biophys. Acta*, 211: 158-168 (1970). The molecular structure of the phosphate-transport protein is provided in Luecke and Quiocho, *Nature*, 347: 402-406 (1990).

The pstS gene belongs to the phosphate regulon whose expression is induced by phosphate starvation and regulated positively by the PhoB protein. The phosphate (pho) box is a consensus sequence shared by, the regulatory regions of the genes in the pho or pst regulon. Over twenty genes are regulated by phosphate, including pstA, pstS, phoE, pstB, phoU, and ugpAB. When the phosphate concentration of the media drops below about from 0.1 $\mu$M to 0.2 mM (Torriani, *Biochim. Biophys, Acta*, 38: 460-469 [1960]), or in a pstS- mutant (Amemura et al., infra), expression of these genes is induced by a regulatory system that requires the positive regulators PhoB and PhoR.

For an overview of the phosphate regulon in *E. coli*, see Shinagawa et al., "Structure and Function of the Regulatory Genes for the Phosphate Regulon in *Escherichia coli*" in *Phosphate Metabolism and Cellular Regulation in Microorganisms*, Torriani-Gorini et al., eds. (American Society for Microbiology, Washington, D.C., 1987), pp. 20-25; Wanner, "Phosphate Regulation of Gene Expression in *Escherichia coli*," in Neidhardt FC et al. (eds.) *Escherichia coli and Salmonella typhimurium: Cellular and Molecular Biology* (American Society for Microbiology, Washington, D.C., 1987) p. 1326-1333; Torriani, *BioEssays*, 12: 371-376 (1990) ; Matin et al., *Annu. Rev. Microbiol.*, 43: 293-316 (1989).

The DNA fragment containing the pstS gene has been isolated from *E. coli* strain K-12 chromosomal DNA. Iwakura et al., *J. Biochem.*, 92: 615-622 (1982). Later, the complete nucleotide sequence of, and amino acid sequence encoded by, the pstS gene and prepstS gene were reported by Magota et al., *J. Bacterial.*, 157: 909-917 (1984). See also Surin et al., supra. The pre-PstS protein contains an extension of peptide composed of 25 amino acid residues at the amino terminus of the PstS protein, which has the general characteristics of a signal peptide. The mature PstS protein is composed of 321 amino acids with a calculated molecular weight of about 34,422-34,427. The regulatory region of the pstS gene contains a characteristic Shine-Dalgarno sequence at an appropriate position preceding the translational initiation site, as well as three possible Pribnow boxes and one −35 sequence. The sequences of the structural pstS gene and promoter region are also described by Surin et al., *Bacterial.*, 157: 772-778 (1984), who identify an alternative promoter region on the basis of homology with the promoter regions of the pstA and pstE genes. The promoter of the pstS gene was also studied by Kimura et al., *Mol, Gen. Genet.* 215: 374-380 (1989).

The function of the PstS protein is to transport inorganic phosphate from the periplasm into the cell, as a phosphate-specific transport protein. The transport is achieved when the PstS protein binds to the phosphate through its phosphate-binding domain. For *E. coli*, this domain includes the backbone residues 10, 11, 38, 140, and 141 and the side chains of residues 10, 38, 56, 135, 139, and 141. Other residues may also indirectly affect phosphate binding, the associated conformational shift from open to closed complex when phosphate is bound to PstS, and/or the associated signaling pathway.

All defined pstS mutations in the PST region were found to lack the periplasmic phosphate-binding protein, so this locus was considered as the structural gene of the binding protein. Levitz et al., *Mol, Gen, Genet.*, 200: 118-122 (1985).

The alkaline phosphatase (phoA) promoter has been used often as a promoter for expressing both homologous and heterologous DNA in bacterial cells. See, e.g., JP 61/280292 published 10 Dec. 1986. In the production of polypeptides utilizing the alkaline phosphatase or pstS promoter cell growth occurs initially with low inorganic phosphate in the medium. These cells utilize the phosphate in the medium so that induction of expression of the gene encoding the polypeptide occurs in late log phase of cell growth as the phosphate content decreases below a threshold value. The cells then starve completely for phosphate, resulting in cessation of growth, a several-fold increase in degradation of cell proteins, so and an inhibition of RNA synthesis. St. John and Goldberg, *J. Bacteriol.*, 143: 1223-1233 (1980). In addition, the extent of expression and rate of protein production cannot be controlled because of the necessity for the near absence of inorganic phosphate in the medium.

Various methods have been explored using the pst regulon to increase expression levels. For example, an expression vector containing a gene coding for PstS bound to a replicon is reported to increase expression levels in bacteria of genes of interest. U.S. Pat. No. 4,703,005 issued 27 Oct. 1987. Additionally, a fusion polypeptide of the sequence PstS-Sc-X-, wherein Sc is a sequence coding for a cleavage site and X is the gene coding for a specified protein, is disclosed in Fr. Pat. Appln. No. 2,599,380 published 4 Dec. 1987.

Mutants of phosphate-specific transport proteins have also been reported. For example, *E. coli* strains have been described that contain pstA mutants prepared by mixing the bacteria with N-nitroso compounds. Israeli Pat. Appl. No. 60714/3 dated 31 Jul. 1980. Also, strains of *E. coli* have been reported that specifically excrete alkaline phosphatase, have a mutation in the pst regulon (including a pstS-type mutation) and are transformed by a plasmid containing an *E. coli* DNA fragment corresponding to the 8.5-minute region of the genetic map. WO 86/04089 published 17 Jul. 1986. *E. coli* PhoA mutants prepared in such strains have also been described. IL 60,714 published 31 Jul. 1980. Mutated alkaline phosphatase enzymes produced by *E. coli* with at least one amino acid mutation having increased enzymatic activity over the wild-type enzyme have been disclosed. EP 441,252 published 14 Aug. 1991.

In addition, the PstS function was examined by analysis of 12 pstS mutants, eight of which had a change of Thr-10 to Ile-10, two of which had a change of Ser-254 to Phe-254, one of which had two changes of Thr-10 to Ile-10 and Gly-140 to Glu-140, and one of which had three changes of Thr-10 to Ile-10, Thr-253 to Ile-253, and Ser-254 to Phe-254. The authors postulated from the results that Thr-10 and Ser-254 are involved in the interaction with the membrane components of the Pst system, whereas Gly-140 is involved in the binding of phosphate, or alternatively, there may be more than one phosphate-binding domain in the phosphate-binding protein, and Thr-10 or Ser-254 may also be involved in phosphate binding. Nakata et al., "Genetic and Biochemical Analysis of the Phosphate-Specific Transport System in *Escherichia coli*," in *Phosphate Metabolism and Cellular Regulation in Microorganisms*, Torriani-Gorini et al., eds., supra, pp. 150–155.

It is an object of the present invention to identify novel nucleic acid molecules encoding specific variants of PstS that, when integrated into the chromosome of bacterial cells as a replacement for the wild-type pstS gene, will allow growth of bacterial cells transformed with DNA encoding a polypeptide of interest under the control of the alkaline phosphatase promoter in the presence of inorganic phosphate at all growth phases.

It is another object to utilize the novel nucleic acid molecules herein to control the transcription rate of nucleic acid encoding a polypeptide of interest and therefore control the extent is of induction of the alkaline phosphatase promoter in bacterial cells.

It is yet another object to minimize proteolysis of polypeptides produced by bacterial cells under transcriptional control of the alkaline phosphatase promoter.

It is still another object to control the strength of induction of the alkaline phosphatase promoter to minimize cell toxicity caused by rapid induction of the promoter.

These and other objects of the invention will be apparent to the ordinary artisan upon consideration of the specification as a whole.

SUMMARY OF THE INVENTION

Accordingly, in one embodiment the present invention provides a nucleic acid molecule encoding an *E. coli* PstS variant selected from the group consisting of T10F PstS, T10L PatS, T10M PstS, T10Y PstS, T10A PstS, T10C PstS, T10G PstS, S38F PstS, D56V PstS, D56A PstS, D56L PstS, D56S PstS, S139T PstS, S139P PstS, S139L PstS, and T141H PstS.

In another embodiment, the invention provides *E. coli* host cells comprising the above nucleic acid molecule under the transcriptional control of the wild-type *E. coli* pstS gene promoter, preferably integrated into the chromosome thereof. These host cells optionally further comprise a nucleic acid molecule encoding a polypeptide of interest under the transcriptional control of the alkaline phosphatase promoter.

In still another embodiment, the invention provides a method for producing a polypeptide of interest comprising culturing bacterial cells that lack their native pstS gene and comprise a nucleic acid molecule encoding a PstS variant having an amino acid variation within the phosphate-binding region of the corresponding native PstS, which nucleic acid molecule is under the transcriptional control of the wild-type pstS gene promoter, and which bacterial cells also comprise a nucleic acid molecule encoding the polypeptide of interest under the transcriptional control of the alkaline phosphatase promoter, wherein the culturing takes place in a culture medium at a concentration of inorganic phosphate in the medium that during all phases of cell growth is above the level at which the cells are starved for phosphate and takes place under conditions that allow expression of the nucleic acid encoding the polypeptide of interest.

Preferably, the pstS variant is homologous to the native pstS gene in the host cells. Also, preferably the bacterial cells are *E. coli* and a hydrophobic residue is substituted for threonine at position 10 or a serine is substituted for aspartic acid at position 56 of the phosphate-binding region of native *E. coli* PstS. Preferably, the amino acid variation in the nucleic acid molecule is a substitution and the nucleic acid molecule is a DNA molecule.

Alternatively, the invention provides a method of controlling the rate of expression of a polypeptide in bacterial cells comprising culturing bacterial cells that lack their native pstS gene and comprise a nucleic acid molecule encoding a PstS variant having an amino acid variation within the phosphate-binding region of the corresponding native PstS, which nucleic acid molecule is under the transcriptional control of the wild-type pstS gene promoter, and which bacterial cells also comprise a nucleic acid molecule encoding the polypeptide of interest under the transcriptional control of the alkaline phosphatase promoter, wherein the culturing is under conditions whereby the concentration of inorganic phosphate in the culture medium is controlled during the production phase of cell growth so that the polypeptide is produced under the transcriptional control of a partially induced alkaline phosphatase promoter.

The PstS variants herein allow the preparation of bacterial host cells that will afford enhanced yield of intact polypeptide. Also, induction at a higher phosphate concentration allows a richer medium to be used, translating to a higher cell density. The method also provides a method of controlling expression of the nucleic acid encoding the polypeptide by controlling the phosphate level at the polypeptide production stage of cell growth.

Furthermore, the mutated PstS protein system allows better regulation of the strength of induction of the alkaline phosphatase promoter so as to prevent cell toxicity, by using slow feeds of phosphate and/or on-line measurement and control of phosphate levels in the supernatant.

BRIEF DESCRIPTION OF THE DRAWINGS

FIGS. 1A–1E collectively illustrate nucleotide sequence and translated amino acid sequence of the pstS structural gene of *E. coli*. (SEQ. ID NO. 1 and SEQ. ID NO. 2, respectively)

FIG. 3A illustrates that overexpression of PstS decreases PhoA induction. The open circles are wild-type W3110 *E. coli* strain 1A2, the large open squares are the pstS- W3110 strain 13G8, the solid circles are the pstS- strain 13G8 transformed with pSB20, a multi-copy plasmid containing the wild-type pstS gene, the diamonds are the T10A PstS mutant on pSB20, the solid squares are the S38A PstS mutant on pSB20, the small open squares are the D56A PstS mutant on pSB20, the solid triangles are the R135A PstS mutant on pSB20, the open triangles are the D137A PstS mutant on pSB20, the x's are the S139A PstS mutant on pSB20, and the +'s are the T141A PstS mutant on pSB20.

FIG. 4 illustrates PhoA induction profiles of multicopy PstS mutants obtained by screening from randomizations of the codons encoding residue Thr10. In this figure the +'s are the T10F PstS mutant, the solid diamonds are the T10G PstS mutant, the x's are the T10C PstS mutant, the open diamonds are the T10F PstS mutant, the solid squares are the T10Y PstS mutant, the small open squares are the T10A PstS mutant, the solid triangles are the T10M PstS mutant, the open circles are the 1A2 wild-type strain, the open triangles are the 13GS pstS- strain, and the large open squares are the pstS- strain transformed with pSB20.

FIG. 6A compares the effects of different mutations at residues Thr10, Asp56, and Thr141 PstS on PhoA induction. The open circles are the 1A2 wild-type strain, the open triangles are the pstS- strain 13G8, the open squares are the PstS- strain transformed with plasmid pSB20, the open diamonds are the T10A PstS mutant, the +'s are the T10M mutant, the solid squares are the T10Y PstS mutant, the x's are the D56A PstS mutant, the solid circles are the D56S PstS mutant, the solid diamonds are the T141A PstS mutant, and the solid triangles are the T141H PstS mutant. FIG. 6B depicts the same data as FIG. 6A, but expands the -10-70 range of the PNPP turnover so that the induction of the mutants can be seen in detail. The symbols used in FIG. 6B are the same as those used in FIG. 6A.

FIGS. 14A-14C collectively depict the nucleotide sequence of the expression cassette and amino acid sequence encoded by the lamb signal sequence and the IGF-I gene in plasmid pLS32Tsc (SEQ. ID NO. 27 and SEQ. ID NO. 28 respectively).

FIG. 16 depicts the nucleotide sequence of the EcoRI-EcoRI fragment (from positions 1149 to 1633) of p200 containing the MF alpha I prepro and IGF-I gene sequences (SEQ. ID NO. 29).

DETAILED DESCRIPTION OF THE PREFERRED EMBODIMENTS

A. Definitions

Figure 2:
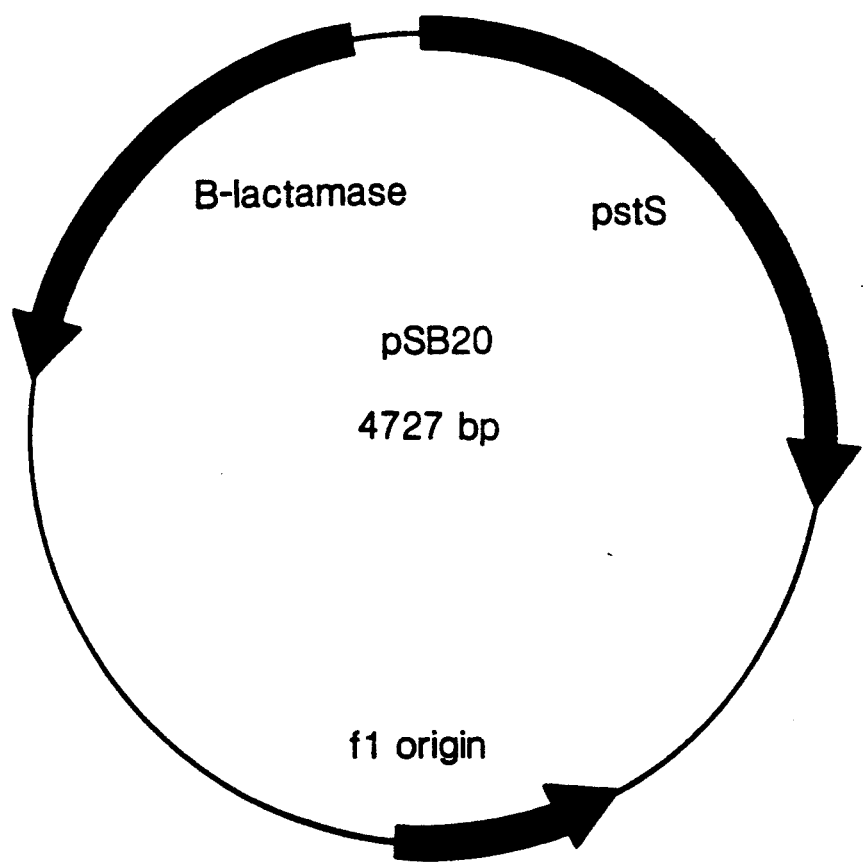
FIG. 2 illustrates the plasmid pSB20 used in generating the pstS mutants.

In general, the following words or phrases have the indicated definition when used in the description, examples, and claims:

The term "PstS" refers to the protein encoded by the pstS gene found in bacterial cells, especially Enterobacteriaceae cells, including *E. coli* cells. This protein is known as the phosphate-binding protein of the bacterial cells and contains a phosphate-binding region.

The "phosphate-binding region" is the region of the protein that binds to inorganic phosphate. This region includes the domain wherein hydrogen bonds form between the two molecules. In *E. coli* PstS this region is:

| Side Chains | Backbone |
|---|---|
| Thr 10 | Thr 10 |
| Ser 38 | Thr 141 |
| Asp 56 | Ser 38 |
| Arg 135 | Gly 140 |
| Ser 139 | Phe 11 |
| Thr 141 | |

This region also includes other residues that indirectly affect phosphate binding, the associated conformational shift from open to closed complex when the phosphate is bound, and/or the associated signaling pathway. Thus, mutations in residues of PstS not directly contacting the phosphate (or proteins truncated by stop codons or frame-shifts) may have similar phenotypes to mutations in residues of PstS that bind directly to the phosphate.

"PstS variants" are defined as molecules in which the amino acid sequence of the corresponding native (wild-type) PstS protein has been modified (by either a predetermined or random mutation) in the phosphate-binding region thereof, in such a way that the PstS protein no longer functions as a repressor at levels of phosphate greater than about 10 μmolar. Furlong, "Osmotic-Shock-Sensitive Transport Systems," in Neidhardt FC et al. (eds.) *Escherichia coli and Salmonella typhimurium: Cellular and Molecular Biology*, Vol. 1 (American Society for Microbiology, Washington, D.C., 1987) p. 768-796, particularly p. 772-773. Thus, the mutation reduces the affinity of the binding protein for phosphate. Amino acid sequence variants of PstS include, for example, deletions from, or insertions or substitutions of, residues within the PstS amino acid sequence shown in FIG. 1. Any combination of deletion, insertion, and substitution may also be made to arrive at the final construct, provided that the final construct possesses the desired property of allowing polypeptide induction by the bacterial host cell at concentrations of phosphate in the medium that are above the starvation level.

The phrase "hydrophobic residues" refers to the residues norleucine, cysteine, methionine, alanine, valine, leucine, tyrosine, phenylalanine, tryptophan, and isoleucine.

"Polypeptide of interest" refers generally to peptides and proteins having more than about 10 amino acids. The polypeptides may be homologous to the bacterial host cell, or preferably, may be heterologous to the host cell, such as yeast polypeptides, or more preferably, mammalian polypeptides. Examples of bacterial polypeptides include, e.g., alkaline phosphatase and β-lactamase. Examples of mammalian polypeptides include molecules such as, e.g., renin, a growth hormone, including human growth hormone, des-N-methionyl human growth hormone, and bovine growth hormone; growth hormone releasing factor; parathyroid hormone; thyroid stimulating hormone; thyroxine; lipoproteins; α1-antitrypsin; insulin A-chain; insulin B-chain; proinsulin; follicle stimulating hormone; calcitonin; leutinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA) ; bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor; receptors for hormones or growth factors; integrin; thrombopoietin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as AFGF and BFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II) ; insulin-like growth factor binding proteins; CD proteins such as CD-3, CD-4, CD-8, and CD-19; erythropoietin; osteoinductive factors; immunotoxins; a bone morphogenetic protein (BMP); somatotropins; an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressing; regulatory proteins; antibodies; and fragments of any of the above-listed polypeptides.

The preferred polypeptides of interest are those that are easily expressed in bacterial cells with a minimum of proteolysis and a maximum in properly refolded or active material and need not be glycosylated for their intended utility. Examples of such mammalian polypeptides include IGF-I, growth hormone, DNase, relaxin, growth hormone releasing factor, insulin, urokinase, immunotoxins, and antigens. Particularly preferred mammalian polypeptides include IGF-I and growth hormone.

"Production phase of cell growth" refers to the period of time during cell growth following induction of the promoter when the polypeptide of interest is being produced.

"Partially induced" as it applies to the alkaline phosphatase promoter refers to a state in which complete induction of the alkaline phosphatase promoter is not achieved, but rather only partial induction thereof. In this way, the rate of transcription of the nucleic acid desired to be expressed is controlled.

The expression "control sequences" refers to DNA sequences necessary for the expression of an operably linked coding sequence in a particular host organism. The control sequences that are suitable for bacteria include the alkaline phosphatase promoter, optionally an operator sequence, and a ribosome-binding site.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The technique of "polymerase chain reaction," or "PCR," as used herein generally refers to a procedure wherein minute amounts of a specific piece of nucleic acid, RNA, and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5'-terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally mullis et al., *Cold Spring Harbor Symp. Quant. Biol.*, 51: 263 (1987); Erlich, ed., *PCR Technology*, (Stockton Press, N.Y., 1989). For a recent review on PCR advances, see Erlich et al., *Science*, 252: 1643–1650 (1991).

As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, "phosphate starvation level" or "level at which cells are starved for phosphate" refers to a concentration of inorganic phosphate (e.g., salts of phosphoric acid such as sodium phosphate, potassium phosphate, or phosphate associated with complex nitrogen sources such as casein hydrolysates or yeast extracts, etc.) in the culture medium so low that the cells are considered deprived of the phosphate ions, leading to a reversible increase in the rate of protein degradation, an inhibition of RNA synthesis, a decrease in cell growth, and a decrease in ATP. This is described further in St. John and Goldberg, supra. This starvation level is to be distinguished from the level of phosphate required for induction/repression of the phoA promoter. Complete starvation is not required to induce this promoter. pstS is thought to be the cells' sensor of phosphate levels and therefore indirectly induces phoA expression. The desired inorganic phosphate concentration for inducing polypeptide production will depend on such factors as the type of polypeptide being produced, the type of host cell, the type of medium, and the culture conditions employed. An exemplary concentration for this purpose is 0.1–10 $\mu$molar.

B. Modes for Carrying Out the Invention

For purposes of this invention, a PstS variant contains one or more amino acid mutations within its phosphate-binding region, and is preferably from *E. coli*. Such variants may be prepared by any means, e.g., recombinant, synthetic, or partially synthetic. Amino acid sequence variants of PstS are suitably prepared by introducing appropriate nucleotide changes into the pstS DNA. Such variants include, for example, deletions from, or insertions or substitutions of, residues within the amino acid sequence shown for *E. coli* PstS in FIG. 1. Any combination of deletion, insertion, and substitution is made to arrive at the final construct, provided that the final construct possesses the desired characteristics. Excluded from the scope of this invention are PstS variants that are not novel and unobvious over the prior art.

For the design of amino acid sequence variants of PstS, the optimum induction characteristics will depend on the location of the mutation site within the phosphate-binding region and the nature of the mutation. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

While the site for introducing an amino acid sequence variation is predetermined, the nature of the mutation per se need not be predetermined. For example, to optimize the performance of a mutation at a given site, random mutagenesis is suitably conducted at the target codon or region and the expressed PstS variants are screened for the optimal induction characteristics.

Amino acid sequence deletions within the phosphate-binding domain of PstS generally will range from about 1 to 5 residues, and typically are contiguous. Contiguous deletions ordinarily are made in even numbers of residues, but single or odd numbers of deletions are within the scope hereof.

Amino acid sequence insertions are intrasequence insertions of single or multiple amino acid residues within the phosphate-binding domain, generally ranging from about 1 to 5 residues, most preferably 1 to 3. Insertions are preferably made in even numbers of residues, but this is not required.

A third group of variants, which are preferred herein, are amino acid substitution variants. These variants have at least one amino acid residue within the phosphate-binding region of the native PstS molecule removed and a different residue inserted in its place.

Substantial modifications in phosphate-binding ability of the PstS protein are accomplished by selecting substitutions that differ significantly in their effect on maintaining (a) the structure of the PstS polypeptide backbone in the area of the substitution, for example, as a sheet or helical conformation, (b) the charge or hydrophobicity of the molecule at the target site, or (c) the bulk of the side-chain. Naturally occurring residues are divided into groups based on common side-chain properties:

(1) hydrophobic: norleucine, cys, met, ala, val, leu, tyr, phe, trp, ile;
(2) neutral hydrophilic: ser, thr;
(3) acidic: asp, glu;
(4) basic: asn, gln, his, lys, arg; and
(5) residues that influence chain orientation: gly, pro.

Preferably, the variants herein are those in which one or more of the amino acid residues positioned at the critical phosphate-binding region of the native counterpart protein is replaced with one or more different amino acids. For *E. coli* pstS variants, preferably residues thr, pro, or leu are substituted for the serine residue at position 139, residue his is substituted for the threonine residue at position 141, residues phe, leu, met, tyr, ala, cys, or gly are substituted for the threonine residue at position 10, and/or residues val, ala, leu, or ser are substituted for the asparagine residue at position 56 of native PstS. The most preferred *E. coli* PstS variants herein are those wherein a hydrophobic amino acid is substituted for the threonine residue at position 10, most preferably T10M PstS and T10Y PstS, and the variants D56S PstS and T141H PstS, using the nomenclature indicated below. Such amino acid changes may also be combined to provide a variant molecule with more than one altered amino acid.

Nucleic acid molecules encoding amino acid sequence variants of PstS are prepared by a variety of methods known in the art. These methods include, but are not limited to, preparation by oligonucleotide-mediated (or site-directed) mutagenesis, alanine-scanning mutagenesis, random mutagenesis, PCR mutagenesis, and cassette mutagenesis of an earlier prepared variant or a nonvariant version of PstS.

Oligonucleotide-mediated mutagenesis represents a preferred method for preparing substitution, deletion, and insertion variants of the pstS gene, although other methods may be utilized as desired. This technique is well known in the art as described by Zoller and Smith, *Nucleic Acids Res.*, 10: 6487 (1982). Briefly, pstS DNA is altered by hybridizing an oligonucleotide encoding the desired mutation to a DNA template, where the template is the single-stranded form of a plasmid or bacteriophage containing the unaltered or native DNA sequence of pstS. After hybridization, a DNA polymerase is used to synthesize an entire second complementary strand of the template that will thus incorporate the oligonucleotide primer, and will code for the selected alteration in the pstS DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci, USA*, 25: 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153: 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, a single-stranded DNA template may be generated by denaturing double-stranded plasmid (or other) DNA using standard techniques.

A useful method for identification of certain residues or regions of the PstS protein that are preferred locations for mutagenesis is called "alanine-scanning mutagenesis," as described by Cunningham and Wells, *Science*, 244: 1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the expressed PstS variants are screened for the optimal combination of desired activity.

For alteration of the native DNA sequence (to generate amino acid sequence variants, for example), the preferred method is the combination of oligonucleotide-directed mutagenesis and random mutagenesis as described by Kunkel et al., *Methods Enzymol.*, 154: 367 (1987). In this method, oligonucleotide-directed mutagenesis is employed to randomize particular codons of the wild-type pstS gene to encode all possible residues. A pool of oligonucleotides with complementary sequence (about 10–15 bases) flanking the codon of choice is used. The codon of choice is replaced with the nucleotides NNS, where N is any nucleotide and S is G or C, to give a pool of oligonucleotides encoding all possible amino acids in 32 codons.

In this preferred method, a pBR322-derived plasmid with a single-stranded origin of replication is prepared as a single-stranded plasmid template in an *E. coli* dut-ung- strain such as CJ236 (Kunkel et al., supra). These two mutations in the strain cause the incorporation of one or more uracil nucleotides into the single-stranded DNA instead of thymine. The random oligonucleotides are annealed, filled in with *E. coli* phage T7 DNA polymerase, ligated, and transformed into a wild-type strain of *E. coli* such as W3110 or strain 13G8 (W3110 tonAΔ PhoS64). The latter strain is pstS minus and derived from CGSC6777 (C75-b), which is derived from C75, described by Amemura et al., *J. Bacter.*, 152: 692–701 (1982). The wild-type strain corrects the uracil misincorporation using the synthetic mutant strand as a template so as to produce about 90% mutants.

DNA encoding PstS mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of PstS. While the following discussion refers to DNA, it is understood that the technique also finds application with RNA. The PCR technique generally refers to the following procedure (see Erlich, supra, the chapter by R. Higuchi, p. 61-70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp ® kits (obtained from Perkin-Elmer Cetus, Norwalk, Conn. and Emeryville, Calif.), and 25 pmole of each oligonucleotide primer, to a final volume of 50 μl. The reaction mixture is overlayed with 35 μl mineral oil. The reaction mixture is denatured for five minutes at 100° C., placed briefly on ice, and then 1 μl Thermus aquaticus (Taq) DNA polymerase (5 units/μl, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.
30 sec. 72° C., then 19 cycles of the following:
30 sec. 94° C.
30 sec. 55° C., and
30 sec. 72° C.

At the end of the program, the reaction vial is removed from the thermal cycler and the aqueous phase transferred to a new vial, extracted with phenol/chloroform (50:50 vol) and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene*, 34: 315 (1985). The starting material is the plasmid (or other vector) comprising the pstS DNA to be mutated. The codon(s) in the pstS DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the pstS DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated pstS DNA sequence.

Nucleic acid encoding the PstS variant may also be chemically synthesized and assembled by any of a number of techniques, prior to expression in a host cell. [See, e.g., U.S. Pat. No. 4,500,707; Balland et al., *Biochimie*, 67: 725–736 (1985); Edge et al., *Nature*, 292: 756–762 (1982)).

For purposes of shorthand designation of the PstS variants described herein, it is noted that numbers refer to the amino acid residue/position along the amino acid sequences of the mature PstS protein. Amino acid identification uses the single-letter alphabet of amino acids, i.e.,

| | | | |
|---|---|---|---|
| Asp | D Aspartic acid | Ile | I Isoleucine |
| Thr | T Threonine | Leu | L Leucine |
| Ser | S Serine | Tyr | Y Tyrosine |
| Glu | E Glutamic acid | Phe | F Phenylalanine |
| Pro | P Proline | His | H Histidine |
| Gly | G Glycine | Lys | K Lysine |
| Ala | A Alanine | Arg | R Arginine |
| Cys | C Cysteine | Trp | W Tryptophan |

| | | |
|---|---|---|
| Val V Valine | Gln Q Glutamine | |
| Met M Methionine | Asn N Asparagine | |

The designation for a substitution variant herein consists of a letter followed by a number followed by a letter. The first (leftmost) letter designates the amino acid in the wild-type, mature PstS protein. The number refers to the amino acid position where the amino acid substitution is being made, and the second (right-hand) letter designates the amino acid that is used to replace the wild-type amino acid. The designation for an insertion variant consists of the letter i followed by a number designating the position of the residue in wild-type, mature PstS protein before which the insertion starts, followed by one or more capital letters indicating, inclusively, the insertion to be made. The designation for a deletion variant consists of the letter d followed by the number of the start position of the deletion to the number of the end position of the deletion, with the positions being based on the wild-type, mature PstS protein. Multiple mutations are separated by a comma in the notation for ease of reading them.

Examples of the nomenclature for E. coli PstS protein are as follows: a substitution variant where the threonine at position 10 of the wild-type PstS protein is replaced with a methionine residue is designated T10M PstS. A substitution variant with multiple substitutions M and S at positions 10 and 56 of the wild-type PstS protein is designated T10M,D56S PstS. An insertion variant where cysteine and valine are inserted after the threonine at position 10 of wild-type PstS is designated iT10CV PstS. A deletion variant where the amino acid (threonine) at position 10 is deleted from the wild-type, mature PstS is designated dT10 PstS. As indicated in the above examples, the notation 'PstS' follows after each mutant.

Most deletions and insertions, and substitutions in particular, are not expected to produce radical changes in the characteristics of the PstS molecule. However, when it is difficult to predict the exact effect of the substitution, deletion, or insertion in advance of doing so, one skilled in the art appreciates that the effect may be evaluated by routine screening assays.

A DNA variant typically may be made by random and/or site-specific mutagenesis of the native PstS-encoding nucleic acid and transfection or integration of the pstS variant gene into the chromosomes of a bacterial host, or by random mutagenesis of a host containing the native pstS gene. The nucleic acid variant may then be screened in a suitable screening assay for the desired characteristic.

For example, in one embodiment, the mutant genes are screened for alkaline phosphatase activity in high phosphate (about 3 mm phosphate) by transforming the mutant pool into a pstS- W3110 strain such as strain 13G8 described above or C75 (Amemura et al., supra) and plating on LB-BCIP-carbenicillin plates. Plasmids are isolated from blue colonies and the pstS gene is then sequenced to determine specific mutations.

Alternatively, single transformants are grown overnight in duplicate 96-well plates containing either high (2-5 mill) or low (0.3 mill) phosphate. Then aliquots are assayed for PhoA activity by PNPP hydrolysis. Mutants with increased activity, particular those with higher activity in high phosphate concentration, are sequenced and further characterized for activity.

Sequenced mutants selected from either screen are further characterized by growing cells in 96-well plates containing a range of phosphate concentrations from 0.02 to 50 mM and assaying aliquots for PhoA activity.

The mutants selected from this screening are integrated into the chromosomal pstS locus to replace the wild-type gene and to be under the transcriptional control of the wild-type PstS promoter. The integrated strains are characterized by assaying PhoA levels.

Those strains meeting this last test can then be evaluated in shake-flask cultures with varying initial phosphate concentrations to assay for the expression of either homologous or heterologous protein products as appropriate. In addition or alternatively, the new organisms can be evaluated in high-cell-density fermentations where different phosphate feeding rates are employed after the initially charged phosphate is depleted. As a final test and optimization, these strains can then be used in a fermentor where phosphate levels can be monitored and regulated on-line. If the polypeptide of interest is homologous to the bacterial cells with the mutated gene, e.g., PhoA, then the cells will be characterized by assaying levels of that polypeptide. If the polypeptide of interest is heterologous to the bacterial cells, the cells are transformed with the nucleic acid encoding this polypeptide and the cells will be assayed for levels of that polypeptide produced under transcriptional control of the phoA promoter.

In the latter application, the phosphate level of the medium in which the altered bacterial host cells are cultured is measured on line (i.e., by continuous sampling), starting with an excess of phosphate (40 mM) in the medium. Then the phosphate level is depleted to about 0.2 to 5 mM phosphate, and the rate of induction of the PhoA promoter is measured by techniques known to those skilled in the art. The preferred PstS mutants are those wherein the polypeptide induction at this concentration of phosphate increases the ultimate yield of polypeptide or increases the relative amount of intact polypeptide or the cell density.

If the nucleic acid encoding the PstS variant is produced outside the bacterial host cell that will ultimately produce the polypeptide of interest, the nucleic acid is introduced into the appropriate bacterial cell using any suitable method, including transfection and transformation by a vector encoding the PstS variant and, preferably, integration into the chromosome of the bacterial cells by any suitable method known in the art. An example of insertion of the pstS gene into the host genome includes that using the E. coli species as host. In this case included in the vector for transformation is a DNA sequence that is complementary to a sequence found in E. coli genomic DNA. Transfection of E. coli with this vector results in homologous recombination with the genome and insertion of the pstS variant gene. The host for this purpose is either pstS minus or has its wild-type pstS gene replaced by the pstS variant gene upon integration thereof.

The bacterial cells containing the mutated pstS gene can inherently carry the polypeptide of interest. For example, alkaline phosphatase is a protein that is homologous to E. coli and can be induced without any further transfection of the cell with vector DNA. For heterologous polypeptides such as, e.g., IGF-I and growth hormone, the heterologous nucleic acid (e.g., cDNA or genomic DNA) is suitably inserted into a replicable vector for expression in the bacterial culture medium under the control of the alkaline phosphatase promoter.

Many vectors are available for this purpose, and selection of the appropriate vector will depend on the size of the nucleic acid to be inserted into the vector and the particular host cell to be transformed with the vector. Each vector contains various components depending on its function (amplification of DNA or expression of DNA) and the host cell with which it is compatible. The vector components for bacterial transformation generally include, but are not limited to, one or more of the following: a signal sequence, an origin of replication, one or more marker genes, and an alkaline phosphatase promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli is typically transformed using pBR322, a plasmid derived from an E. coli species (see, e.g., Bolivar et al., Gene, 2: 95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of the selectable marker genes.

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide contains an alkaline phosphatase promoter that is recognized by the host bacterial organism and is operably linked to the nucleic acid encoding the polypeptide of interest. This promoter is inducible, i.e., it initiates increased levels of transcription from DNA under its control in response to a decreased concentration of inorganic phosphate in the culture medium. The phoA promoter can be removed from the bacterial source DNA by restriction enzyme digestion and inserted into the vector containing the desired DNA.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform E. coli K12 strain 294 (ATCC 31,446) or other strains and successful transformants are selected by ampicillin or tetracycline resistance where appropriate. Plasmids from the transformants are prepared, analyzed by restriction endonuclease digestion, and/or sequenced by the method of Sanger et al., Proc. Natl. Acad. Sci. USA, 74: 5463-5467 (1977) or Messing et al., Nucleic Acids Res., 9: 309 (1981) or by the method of Maxam et al., Methods in Enzymology, 51: 499 (1980).

The bacterial host cells used for expressing the vectors encoding the polypeptide of interest are those that in nature contain a native pstS gene. For the method herein that native gene is lacking and is replaced by the pstS variant gene, which is preferably homologous to the native pstS gene normally present in the host cells. Suitable bacteria for this purpose include enbacteria, especially Enterobacteriaceae, where the pstS gene is thus far found. Examples of bacteria belonging to Enterobacteriaceae include Escherichia, Enterobacter, Erwinia, Klebsiella, Proteus, Salmonella, Serratia, and Shigella. One preferred E. coli host is E. coli 294 (ATCC 31,446), although other strains such as E. coli B, E. coli X1776 (ATCC 31,537), and E. coli W3110 (ATCC 27,325) are suitable. These examples are illustrative rather than limiting. Mutant cells of any of the above-mentioned bacteria may also be employed. It is, of course, necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYA177, or pKN410 are used to supply the replicon.

E. coli strain W3110 is a particularly preferred parent host because it is a common host strain for recombinant DNA product fermentations. Preferably, the host cell should secrete minimal amounts of proteolytic enzymes. For example, strain W3110 may be modified to effect a genetic mutation in the genes encoding proteases, with examples of such hosts including E. coli W3110 strain 9E4, which has the complete genotype tonA ptr3, the preparation of which is described below, and E. coli W3110 strain 27C7, which has the complete genotype tonAΔ ptr3 phoAΔE15 Δ(argFlac)169 ompTΔ degP41-kan. Strain 27C7 was deposited on 30 Oct. 1991 in the American Type Culture Collection as ATCC No. 55,244. Alternatively, the strain of E. coli having mutant periplasmic protease disclosed in U.S. Pat. No. 4,946,783 issued 7 Aug. 1990 may be employed.

Host cells are transformed with the above-described expression vectors of this invention and cultured in conventional nutrient media modified as appropriate for inducing the alkaline phosphatase promoter.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for bacterial cells that contain substantial cell-wall barriers. Another method for transformation employs polyethylene glycol/DMSO, as described in Chung and Miller, *Nucleic Acids Res.*, 16: 3580 (1988)

Bacterial cells used to produce the polypeptide of interest of this invention are cultured in suitable media in which the alkaline phosphatase promoter can be partially or completely induced as described generally, e.g., in Sambrook et al., supra. The culturing need never take place in the absence of inorganic phosphate or at phosphate starvation levels. At first, the medium contains inorganic phosphate in an amount above the level of induction of protein synthesis and sufficient for the growth of the bacterium. As the cells grow and utilize phosphate, they decrease the level of phosphate in the medium, thereby causing induction of synthesis of the polypeptide.

Any other necessary supplements besides carbon, nitrogen, and inorganic phosphate sources may also be included at appropriate concentrations introduced alone or as a mixture with another supplement or medium such as a complex nitrogen source.

If the polypeptide is alkaline phosphatase, the composition of the carbon, nitrogen, and phosphate sources of the nutrient medium is preferably such that during the phase of intensive polypeptide accumulation the glucose content of the medium is approximately 0%, the phosphate content is more than about 0.5 mM and less than about 5 mM, depending on the PstS variant employed, and the nitrogen concentration is not more than about 30 μg/ml. Glucose feeding is preferably carried out during the transitional phase. The fermentation medium is preferably subjected to intensive mixing and the fermentation is preferably carried out at about 25°–40° C., more preferably about 37° C.

Gene expression may be measured in a sample directly, for example, by conventional northern blotting to quantitate the transcription of MRNA. Thomas, *Proc. Natl. Acad, Sci, USA*, 77: 5201-5205 (1980). Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

The polypeptide of interest preferably is recovered from the periplasm or culture medium as a secreted polypeptide, although it also may be recovered from host cell lysates when directly expressed without a secretory signal.

It is often preferred to purify the polypeptide of interest from recombinant cell proteins or polypeptides to obtain preparations that are substantially homogeneous as to the polypeptide of interest. As a first step, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane bound, is soluble, or is present in an aggregated form. The polypeptide thereafter is solubilized and folded, if necessary, and is purified from contaminant soluble proteins and polypeptides, with the following procedures being exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; and gel filtration using, for example, Sephadex G-75.

The invention herein also provides a method for controlling the alkaline phosphatase promoter so that it is only partially induced, so that one can regulate the expression rate of the polypeptide. This was not achievable in the past since the inorganic phosphate level had to be extremely low to induce the promoter and it is not practical to control such low concentrations. With organisms having pstS protein with reduced affinity for phosphate, the concentration of inorganic phosphate is suitably controlled by controlling the feed rate into the medium of inorganic phosphate or of a source containing inorganic phosphate such as a complex nitrogen source.

The following examples are offered by way of illustration and not by way of limitation. The disclosures of all literature references cited in the specification are expressly incorporated herein by reference.

EXAMPLE I

Preparation and Characterization of Mutant Strains

Preparation of Mutant Strains

The polymerase chain reaction (PCR) described above employing the GeneAmp kit from Perkin-Elmer Cetus was used to create a 1.3-Kb DNA fragment containing the pstS gene with its own promoter. The published sequence of the pstS gene (Surin et al., 1984, supra, and Magota et al., supra; shown in FIG. 1) was used to design the following oligonucleotides as primers for the PCR. Underlined nucleotides were added to the natural pstS sequence to introduce restriction sites (EcoRI and AvaI, respectively) for cloning:

5'- G GAA TTC TGT CAT CTC TTC GTT AT (SEQ. ID NO. 3)

5'- CTG CCC GAG CCA TAA GTT ACT CTT CAG (SEQ. ID NO. 4)

Chromosomal DNA was prepared from *E. coli* strain W3110 essentially as described by Silhavy et al., *Experiments with Gene Fusions* (Cold Spring Harbor Laboratory, New York, 1984). The PCR products were extracted with phenol/chloroform, ethanol precipitated, cut with EcoRI and AvaI (New England Biolabs), then isolated from a 1% low melt temperature agarose gel along with the backbone of a similarly cut plasmid phGHr. Fuh et al., *J. Biol. Chem.*, 265: 3111-3115 (1990). The fragments were ligated with T4 DNA ligase cleotides encoding all possible amino acids in 32 codons.

TABLE I

Sequences of Oligonucleotides used in Mutagenesis

| Mutant Designation | |
|---|---|
| Alanine Substitutions | |
| T10A | 5'-G ACA GGT GCA <u>GGC GCC GCC TCC CCT GC</u> (SEQ. ID NO. 5) |
| S38A | 5'-CAG GGT ATC GGT GG<u>C TCG GGT</u> GGC GTA A (SEQ. ID NO. 6) |
| D56A | 5'-TTT GGT GCC T<u>CT GCA GCG</u> CCG CTG T (SEQ. ID NO. 7) |
| R135A | 5'-GCT GTA GTA CGC GC<u>T GCA GAT</u> GGC T (SEQ. ID NO. 8) |
| D137A | 5'-GTA CGC CGC G<u>CT GCA GGC</u> TCC GGG A (SEQ. ID NO. 9) |
| D139A | 5'-C GCA GAT <u>GGC GCC</u> GGG ACT TC (SEQ. ID NO. 10) |
| T141A | 5'-GAT GGC TCC <u>GGC GCC</u> TCC TTC GCT T (SEQ. ID NO. 11) |
| Randomizations | |
| T10 | 5'-G ACA GGT GCA <u>GGC GCC</u> NNS TTC CCT GCG CCG (SEQ. ID NO. 12) |
| S38 | 5'-CAG GGT ATC GGT NNS TCC GGT GGC GTA (SEQ. ID NO. 13) |
| D56 | 5'-GTT GAT TTT <u>GGC GCC</u> TCT NNS GCG CCG CTG TCT (SEQ. ID NO. 14) |
| S139 | 5'-CGC GCA GAT GGC NNS GGG ACT TCC T (SEQ. ID NO. 15) |
| T141 | 5'-GAT GGC TCC GGG NNS TCC TTC GCT T (SEQ. ID NO. 16) |

(New England Biolabs) to obtain the plasmid pSB20 shown in FIG. 2. pSB20 is a derivative of pBR322 that has an origin of replication from phage f1 (Fuh et al., supra), and ~1320 bp of the *E. coli* pstS gene including its promoter and terminator. pSB20 was transformed into *E. coli* strain 13G8 described above, and spread onto LB-BCIP plates (Sigma) plus carbenicillin (50 μg/ml). White colonies indicated complementation of the chromosomal pstS mutation by the plasmid encoding PstS. DNA sequencing (Sanger et al., supra) of the pstS gene on the recovered plasmid agreed with the published sequence.

Oligonucleotide-directed mutagenesis as described in Zoller and Smith, supra, was combined with alanine-scanning mutagenesis (Cunningham and Wells, supra) and random oligonucleotide synthesis using the technique of Kunkel et al., supra, to produce the mutants employed in this example. These methods were used with the oligonucleotides shown in Table I to change the codons of the wild-type pstS sequence for the appropriate residues (bold) to alanine or to randomize to encode all possible residues (N is G, A, T, or C; S is G or C) and introduce new restriction sites (underlined). The presence of all mutations was confirmed by DNA sequencing. A pool of oligonucleotides with complementary sequencing (10-15 bases) flanking the codon of choice was used. The codon of choice was replaced with NNS in the synthesis to produce a pool of oligonu- The single-stranded plasmid template was prepared in an *E. coli* dut- ung- strain CJ236 as described by Kunkel et al., supra. The mutations in this strain lead to the incorporation of one or more uracil nucleotides into the single-stranded DNA instead of thymine. Each of the random oligonucleotides from the pool described above were annealed, filled in with *E. coli* phage T7 DNA polymerase, ligated, and transformed into strain 13G8. The wild-type strain corrects the uracil misincorporation using the synthetic (mutant) strand as a template, to give about 90%, mutants.

The random mutants were screened for PhoA activity in high phosphate (about 3 mM Pi) by transforming the mutant pool into the pstS- W3110 strain 13G8 and plating on LB-BCIP-carbenicillin plates. Plasmids were isolated from blue colonies and the pstS gene was sequenced to determine specific mutations. Alternatively, as described below, single transformants were grown overnight in duplicate 96-well plates containing either high (2-5 mm) or low (0.3 mM) phosphate, then aliquots were assayed for PhoA activity by hydrolysis of PNPP (Sigma). Mutants with increased activity were sequenced and further characterized.

The mutant pstS genes selected from the first screenings, i.e., T10F PstS, T10L PstS, T10M PstS, T10Y PstS, T10A PstS, T10C PstS, T10G PstS, S38F PstS, D56V PstS, D56A PstS, D56L PstS, D56S PstS, S139T PstS, S139P PstS, S139L PstS, and T141H PstS, were further characterized by growing the cells in 96-well plates containing 0.2 ml/well of a minimal media [0.4% glucose, 1.6 mm $MgSO_4$, 20 mM $NH_4Cl$, 50 mM KCl, 20 mM NaCl, 120 mM triethanolamine-HCl (pH 7.4)] with an appropriate concentration of added $KH_2PO_4$ from 0 to 50 mM. Cell growth was monitored by measuring the absorbance at 620 nM. The cells were pelleted after overnight growth at 37° C. with shaking, resuspended in 0.2 ml of 0.15M NaCl, then aliquots were diluted 1:10 into another 96-well plate containing 1M Tris-HCl (pH 8.0), 1 mM PNPP, and 1% sodium dodecyl sulfate (SDS). Alkaline phosphatase activity was determined as the hydrolysis rate of the chromogenic substrate PNPP by the increase in absorbance at 405 nm. PhoA activity is normalized for cell growth by expressing the change in $OD_{405}/min./OD_{620}$.

The mutant pstS genes encoding T10M, T10Y, D56S, and T141H were integrated into the *E. coli* chromosome at the pstS locus to replace the wild-type pstS gene by using a polA strain essentially as described in Gutterson and Koshland, *Proc. Natl. Acad. Sci. USA*, 80: 4894-4898 (1983) (See FIG. 1 thereof.)

The method makes use of the fact that ColE1-derived plasmids such as pBR322 require DNA polymerase I (the polA gene product) to replicate extrachromosomally. The polA strain A401 (Russel and Holmgren, *Proc. Natl. Acad, Sci.*, 85: 990–994 [1988]) was transformed (Chung and Miller, supra) to carbenicillin resistance with the plasmid clone containing the mutant pstS gene of interest. Homologous recombination between the cloned and chromosomal pstS genes leads to integration of the entire plasmid into the chromosomal pstS gene. Recombination can occur to either the left or right of the mutation, giving rise to one of two possible chromosomal DNA structures with integrated plasmid. The plasmid integrates are obtained by selection for carbenicillin resistance.

Integration into the pstS gene was confirmed by P1 cotransduction (Silhavy et al., supra) of carbenicillin resistance with the tetracycline resistance genes of Tn10 insertions located near the pstS gene (zie-296::Tn10 and ilv-500::Tn10). Singer et al., *Microbiol. Revs.*, 53: 1–24 (1989). P1 transduction was then used to transfer the integrated plasmid into the wild-type strain W3110 by selection for carbenicillin. The plasmids will be free to replicate and resolve from the chromosome leaving either the wild-type or mutant pstS gene in the chromosome and the opposite on the freely replicating plasmid. These transductants were grown on LB broth containing 100 μg/ml of santonin to cure the cells of the resolved plasmids (Bharathi and Polasa, *FEMS Microbial. Letts.*, 68: 213–216 [1990]), then plated on LB-BCIP plates. Blue colonies were isolated that contain the mutant pstS gene in the chromosome and are plasmid-free (carbenicillin sensitive).

Screening of Mutant Strains

Expression of PhoA activity was used to determine the effects of the pstS mutations on induction of the phosphate-regulated genes. FIGS. 3–7 show the induction of PhoA activity in response to varying the phosphate concentration in the growth media. In wild-type pstS+ cells, the phoA gene is repressed until the initial phosphate concentration drops below 0.4 mM. Overproduction of PstS in cells with the pstS gene on a pBR322-derived plasmid drastically reduced the level of PhoA induction, but a similar profile was obtained.

Alanine substitutions at each of the six side-chains proposed to interact with the bound phosphate had little effect on this induction profile. Substitution of Thr10, Ser38, or Asp56 with alanine lead to some PhoA expression at higher Pi concentration than wild-type, but not a full induction (FIG. 3).

Figure 3B:
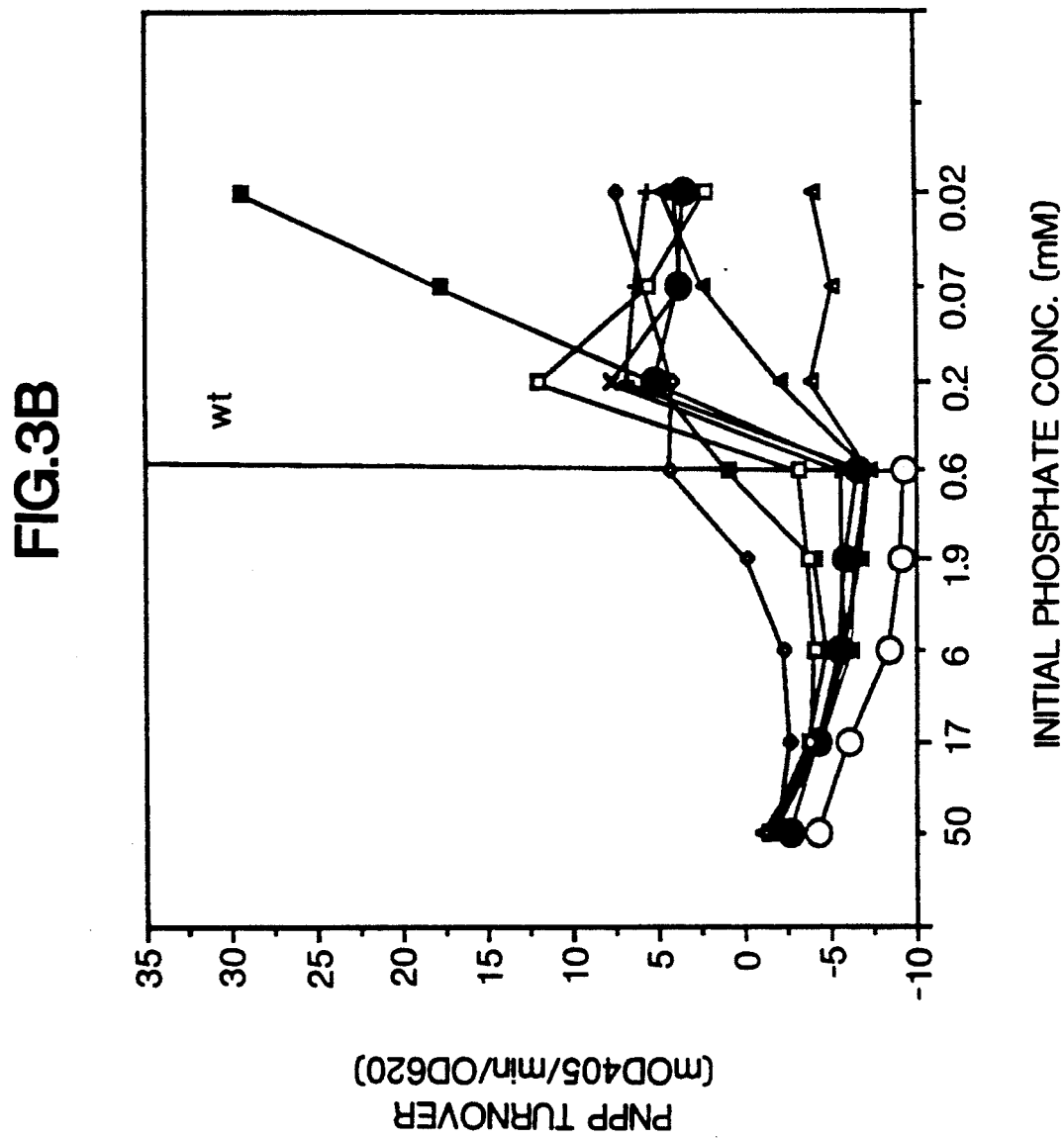
FIG. 3B represents the same data as FIG. 3A but expands the -10-35 range of the p-nitrophenylphosphate (PNPP) turnover so that the induction of the mutants can be seen in detail. The symbols in FIG. 3B are the same as those in FIG. 3A.

FIG. 3A shows that overexpression of PstS by the wild-type strains W3110 and 13G8 decreased PhoA induction. FIG. 3B shows PhoA specific activity in various pstS alanine mutant strains, with the highest PNPP turnover rate as phosphate concentration in the media is increased being the best for purposes of this invention. T10A appeared to be the highest at high phosphate concentrations.

The crystal structure shows that the side chain of Asp137 is hydrogen bonded with the Arg135 side chain and appears to orient Arg135 toward the bound $PO_4$. To test the importance of this interaction in $PO_4$ binding, Asp137 was also substituted with alanine. Surprisingly, removal of either side chain appeared to have little effect on $PO_4$ binding in this system.

Since the alanine substitutions had little effect on PhoA induction at varying phosphate levels, it was reasoned that substitution of these residues with larger side chains would have larger effects by sterically hindering the binding of phosphate.

The codons encoding residues Thr10, Ser38, Asp56, Ser139, and Thr141 were randomized one at a time to encode pools of all residues. These pools were screened for increased PhoA activity after growth in low- and high-phosphate media. Table II shows the specific missense mutations in the pstS genes from blue colonies and the number of times they were isolated.

TABLE II

| Amino Acid Substitutions of Sequenced pstS Missense Mutations | |
| --- | --- |
| Thr10 | Asp56 |
| Ala | Ala (7) |
| Met | Val (4) |
| Phe (2)[a] | Leu (4) |
| Leu (6) | Ser |
| Tyr | Ser139 |
| Cys | Thr (6) |
| Gly | Pro (5) |
| Ser38 | Leu |
| Phe | Thr141 |
| | His |

[a]Numbers in parentheses refer to the number of a particular mutation was isolated.

FIG. 4 shows PhoA induction profiles of multicopy PstS mutants randomized at residue Thr10 and isolated from the screening. Of the mutants, T10Y and T10M appeared to have the highest PNPP turnover rate.

Figure 5:
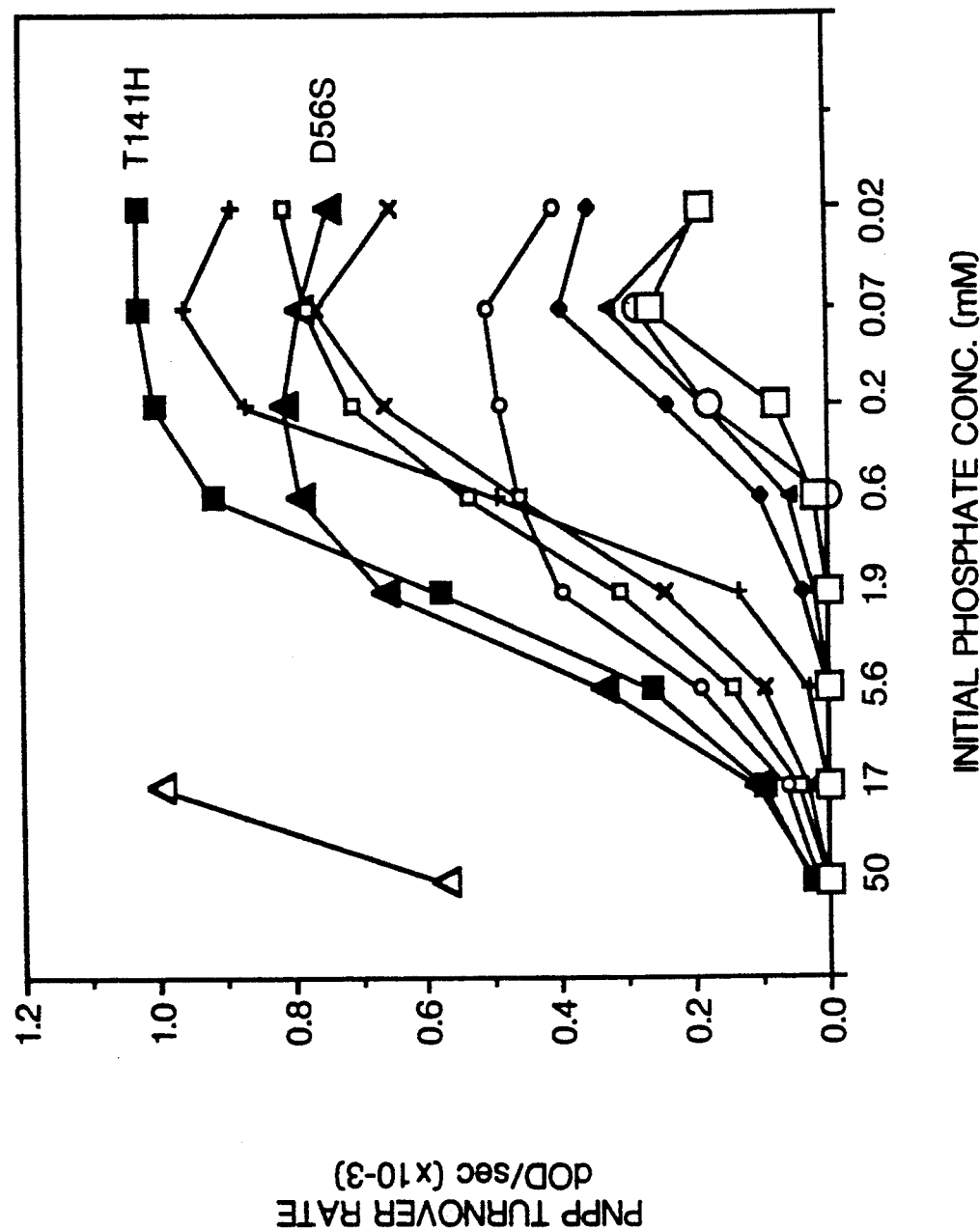
FIG. 5 illustrates PhoA induction profiles of more multicopy PstS mutants obtained by screening random mutant libraries of Ser38, Asp56, Ser139, and Thr141. In this figure, the +'s are the S139T PstS mutant, the diamonds are the S139L PstS mutant, the solid squares are the T141H PstS mutant, the large solid triangles are the D56S PstS mutant, the x is the D56A PstS mutant, the small open squares are the D56V PstS mutant, the small open circles are the D56L PstS mutant, the small solid triangles are the S38F PstS mutant, the large open circles are the 1A2 wild-type strain, the open triangles are the 13G8 pstS- strain, and the large open squares are the pstS- strain transformed with pSB20.

FIG. 5 illustrates PhoA induction profiles of more multicopy PstS mutants obtained by screening randomizations of codons encoding residues Ser38, Asp56, Ser139, and Thr141. Of these mutants, D56S and T141H appeared to have the highest PNPP turnover rate at higher phosphate concentrations.

As with FIG. 3A, FIG. 6A shows that overexpression of PstS decreased PhoA induction. FIG. 6B shows various randomized pstS mutants, with T141H and D56S having an increased PNPP turnover rate at high phosphate concentrations.

Figure 7:
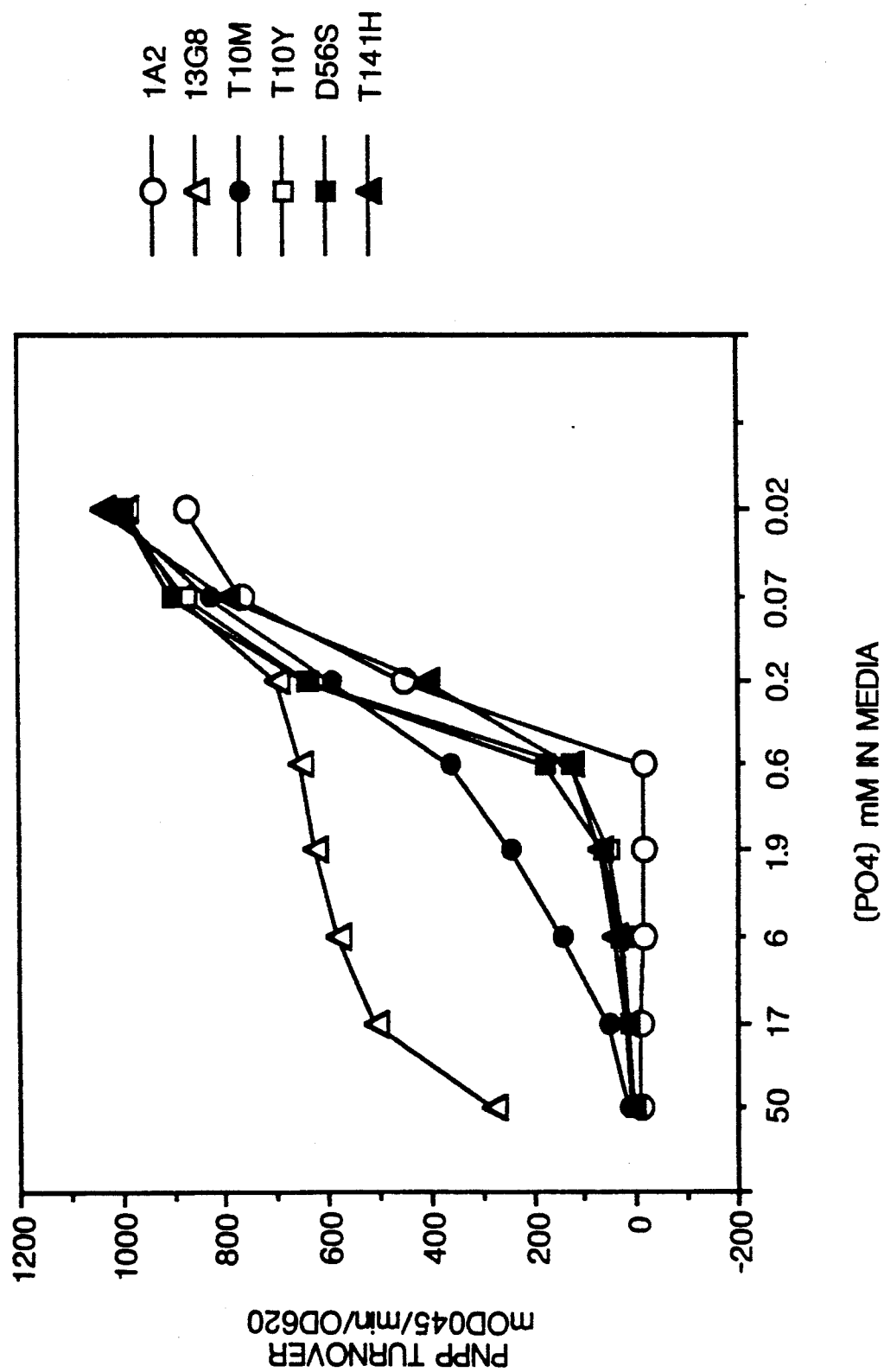
FIG. 7 illustrates PhoA induction profiles of single-copy PstS chromosome mutant strains, where the open circles are the 1A2 wild-type W3110 *E. coli* strain, the open triangles are the pstS-mutant 13G8, the solid circles are the T10M PstS mutant, the open squares are the T10Y PstS mutant, the solid squares are the D56S PstS mutant, and the solid triangles are the T141H PstS mutant.

FIG. 7 demonstrates PhoA induction profiles of single-copy pstS mutant strains with the mutation integrated into the chromosome. These mutants (T10M PstS, T10Y PstS, D56S PstS, and T141H PstS) all lead to PhoA induction at higher phosphate concentrations compared to the wild-type W3110 strain, but are still regulated by yet higher phosphate concentrations, allowing the system to-be controlled.

EXAMPLE II

Shake-Flask E2Meriments with Mutant Strains

Strains Employed

The starting *E. coli* K-12 host strain 9E4 (W3110tonA ptr3) was constructed in multiple steps using techniques involving transductions with phage Plkc, derived from P1 [J. Miller, *Experiments in Molecular Genetics* (Cold Spring Harbor, N.Y.: Cold Spring Harbor Laboratory, 1972)), and transposon genetics [Kleckner et al., *J. Mol. Biol.*, 116: 125–159 (1977)).

The starting host used was *E. coli* K12 W3110, which is a K12 strain that is F-, λ- Bachmann, *Bact. Rev.*, 36:525–557 (1972); Bachman, "Derivatives and Genotypes of Some Mutant Derivatives of *Escherichia coli* K-12," p. 1190–1219, In F. C. Niedhardt et al., ed., *Escherichia coli and Samonella typhimurium: Cellular and Molecular Biology*, vol. 2, American Society for Microbiology, Washington, D.C. (1987)).

First, the tonA gene (fhuA) [Kadner et al., *J. Bact.*, 143: 256–264 (1980), Bachmann, Microbial. Rev,, 47: 180–230 (1983), Bachman, "Linkage Map of *Escherichia coli* K-12," edition 7, p. 807–876, in F. C. Niedhardt et al., ed., "*Escherichia coli and Salmonella tryphimurium: Cellular and Molecular Biology*, Vol. 2, American Society for Microbiology, Washington, D.C., 19871 was deleted from W3110 by the insertion and subsequent imprecise excision of a TN10 transposon into the tonA gene.

In the first step of this procedure, *E. coli* W3110 was transduced with λ::TN10 to generate a TN10 hop pool of *E. coli* W3110 [Kleckner et al., supra].

The *E. coli* W3110::Tn10 hop pool was grown in L broth at 37° C. to a cell density of about $1 \times 10^9$/ml. A total of 0.5 ml of the culture was centrifuged and the pellet wall resuspended in 0.2 ml of a λphi80 lysate containing $7.0 \times 10^9$ pfu. The phage was allowed to adsorb for 30 minutes at 37° C. The suspension was then spread on EMB plates supplemented with tetracycline (15 μg/ml). After an overnight incubation at 37° C., the colonies were pooled in 3 ml of L broth, grown overnight at 37° C., washed twice, and resuspended in L broth. A bacteriophage Plkc lysate was made on this culture [Miller, J. H., *Experiments in Molecular Biology*, supra, page 304].

*E. coli* AT982 (no. 4546, *E. coli* Genetic Stock Center, New Haven, Conn.) was transduced to tetracycline resistance by this Plkc lysate. Transductants were selected on L broth plates supplemented with tetracycline (15 μg/ml) and 40 μg/ml diaminopimelic acid (dap). The resulting transductants were screened for tetracycline resistance and the regeneration of the dap gene (dap+, tet ®) . Transductants with the dap+, tet ® genotype were then tested for λphi80 resistance.

Plkc lysates were then made on several dap+, tet ®, λphi80-resistant strains. The lysates were used to transduce *E. coli* W3110 to tetracycline resistance. The transductants were screened and selected for λphi80 resistance.

Tetracycline-sensitive isolates were selected from the W3110 tonA::Tn10-λphi80R transductants. [Maloy and Nunn, *J. Bacterial.*, 145: 1110 (1981)). These isolates were checked for λphi80 resistance and tetracycline sensitivity after single colony purification.

DNA was isolated from several tetracycline-sensitive λphi80-resistant mutants and digested with SstII. The SstII-digested DNA was characterized by the Southern blot procedure using radioactively labeled and SstII-digested λ::TN10 DNA as a probe to determine if the TN10 had been excised [Davis et al., *Advanced Bacterial Genetics* (Cold Spring Harbor Laboratory, New York, 1980)]. One of the tetracycline-sensitive isolates was shown to have lost two of the TN10 hybridization bands as compared to the hybridization between DNA from the λ::TN10 and the parental W3110 tonA::Tn10λphi80R. A third hybridization band had an altered mobility, indicating that a deletion caused by the imprecise excision of Tn10 had occurred.

SDS-gel electrophoresis of outer membrane preparations from the strain with an imprecise TN10 excision revealed that the band assumed to be the protein encoded by tonA had an altered electrophoretic mobility as compared to the wild-type protein encoded by the tonA gene. The resulting protein was non-functional as a λphi80 phage receptor protein. A second independent strain that also had undergone imprecise excision of TN10 showed no protein encoded by tonA on the SDS gel.

Neither of these strains demonstrated reversion to tetracycline resistance or to λphi80 susceptibility, indicating that there was an imprecise excision of all or part of the Tn10 transposon together with either a partial or complete deletion of the tonA gene. Thus, the protein encoded by the tonA gene (MW 78,000) was eliminated from the outer membrane, rendering the W3110 tonA strain resistant to several bacteriophages. The resulting strain, designated 1A2, is resistant to bacteriophages T1 and φ80.

The ptr3 gene [Cheng et al., *J. Bacterial.*, 140: 125–130 (1979)] was introduced into strain 1A2 as follows. First, the thyA8 mutation was isolated in 1A2 by selecting for trimethoprim resistance to form strain 9E1. Then the argA81::tn10 locus was transported from 9D9 (obtained from B. Bachman, *E. coli* Genetic Stock Center, New Haven, Conn.) into 9E1 by transduction with phage Plkc to form 9E3. The ptr3 locus is between thyA8 and argA81. Transduction with P1 phage grown on a ptr3 mutant [9D7, *J. Bact.*, 140: 125 (1979)] resulted in the introduction of the ptr3 mutation simultaneously with the conversion of thyA8 and argA81::Tn10 to wild-type loci. This strain, designated 9E4, lacks the periplasmic protease III. The conclusion that the ptr3 mutation is included in 9E4 is supported by strongly improved IGF-I accumulation in the resultant strain.

Strains derived from 9E4 with known mutations in the pstS gene were produced as described in Example I, and are given catalog numbers as indicated below:

| Catalog Number | Description |
| --- | --- |
| 9E4 | *E. coli* W3110 tonA prt3 |
| 39B4 | *E. coli* W3110 tonA prt3 pstS (T10M) |
| 39B5 | *E. coli* W3110 tonA prt3 pstS (T10Y) |
| 39B6 | *E. coli* W3110 tonA prt3 pstS (T141H) |
| 39B7 | *E. coli* W3110 tonA prt3 pstS (D56S) |

Expression Vector Construction

The above strains were transformed with the IGF-I expression plasmid pBKIGF-2 using standard transformation techniques. The transcriptional and translational sequences required for expression of the IGF-I gene in *E. coli* are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamb signal sequence or alternatively by the STII signal sequence. The majority of rhIGF-I is found in the cell periplasmic space. Plasmid pBKIGF-2 confers tetracycline resistance upon the transformed host.

Plasmid pBKIGF-2 was constructed in several steps using as intermediate plasmids pLS32Tsc, pLBIGFTsc, pLS33Tsc, and pRanTsc.

Step A: DLS32TSC

Step 1: DLS32

Figure 8:
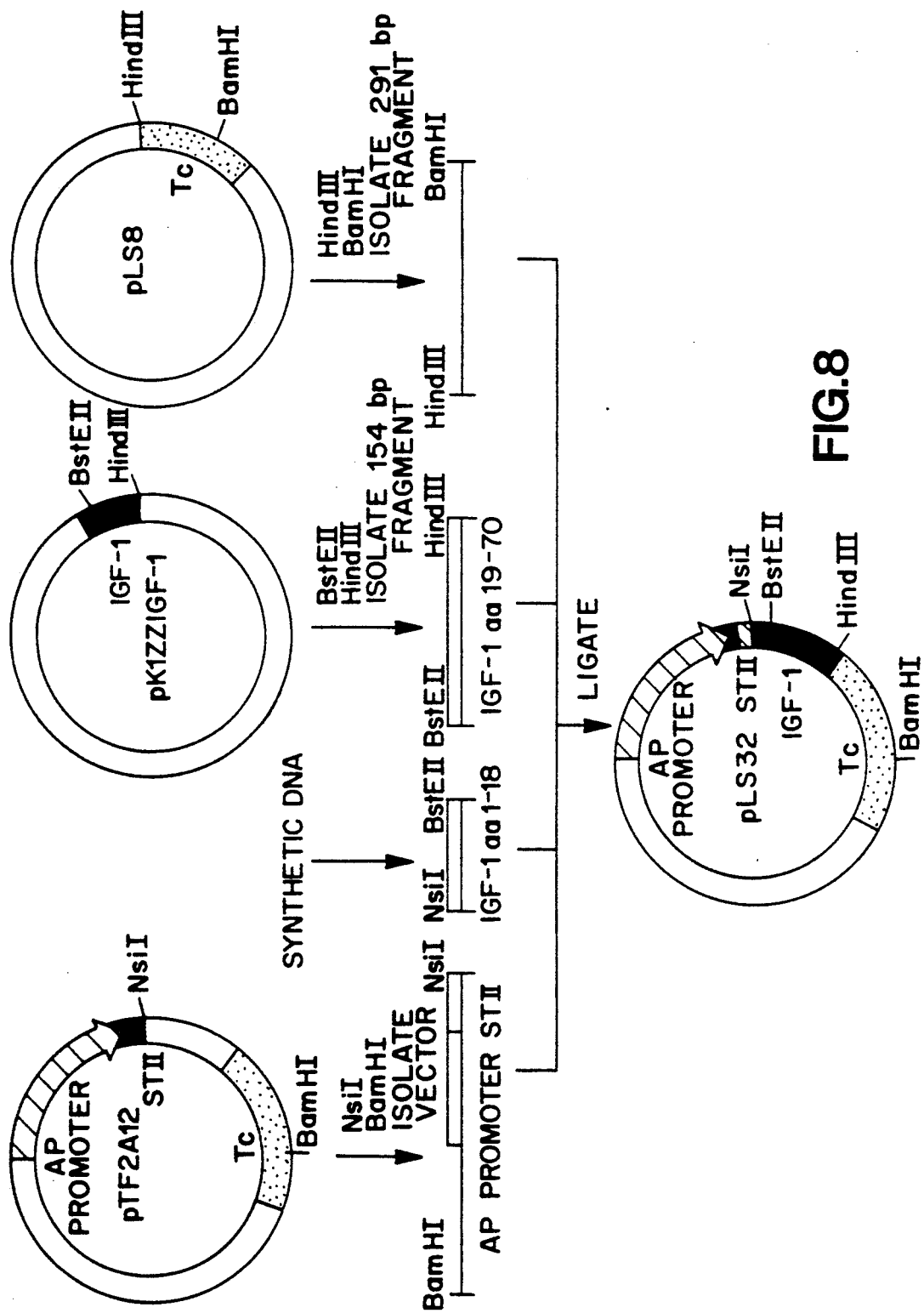
FIG. 8 depicts the construction of plasmid pLS32, an intermediate plasmid in preparing pLS32Tsc, which contains a gene encoding IGF-I and is in turn used to prepare pBKIGF-2, the expression vector encoding IGF-I used in the examples below.

The plasmid pLS32 results in the fusion of the IGF-I coding sequence to the coding sequence of the heat-stable enterotoxin II (STII) signal sequence. It was prepared by ligating together four DNA fragments as shown in FIG. 8. The first of these was the vector pTF2A12 [Paborsky et al., *Biochemistry*, 28: 8072-8077 (1989)] from which the small NsiI-BamHI fragment containing the tissue factor gene had been removed. The STII signal sequence is described by Picken et al.,

```
5' - CTAGAATTATGATGATTACTCTGCGCAAACTTCCTCTGGCGGTTGCC
3' - TTAATACTACTAATGAGACGCGTTTGAAGGAGACCGCCAACGGCA
```

*Infect. Immun.*, 42: 269-275 (1983).

The second fragment was a 55-bp synthetic duplex encoding the first 18 amino acids of mature IGF-I. This duplex has the following sequence:

```
5' - GGTCCCGAAACTCTGTGCGGTGCTGAACTGGTTGACGCTCTGCAGTTTGTTTGCG - 3'
3' - ACGTCCAGGGCTTTGAGACACGCCACGACTTGACCAACTGCGAGACGTCAAACAAACGCCACTG - 5'
```

(SEQ. ID NOS. 17 and 18, respectively)

The third piece in the ligation was a 154-bp BstEII-HindIII fragment from pK1ZZIGF-I encoding the remaining amino acids 19-70 of IGF-I. pK1ZZIGF-I is a kanamycin-resistant plasmid containing a lac promoter attached to a Protein A promoter, which is in turn connected to a Protein A signal, fused to two consensus Z regions from Protein A that bind IgGs and secrete proteins, attached using two codons encoding an Asn-Gly interface to a synthetic IGF-I gene. It also contains an F region to give high copy number. This plasmid is similar to PZZ-IGF-I shown in FIG. 6 of and described in EP Pub. No. 230,869 published 5 Aug. 1987, where the ampicillin gene is replaced by a kanamycin gene.

The last fragment was a 291-bp HindIII-BamHI fragment from the plasmid PLS8. This last fragment is simply the coding sequence for the start of the tetracycline gene of pBR322 [Sutcliffe, *Cold Spring Harbor Symposia On Quantitative Biology*, 43: 77-90 (1978)] in which a HindIII restriction site was engineered immediately upstream of the methionine start codon.

The resulting plasmid, pLS32, efficiently expresses and secretes rhIGF-I to the media. The following two construction steps were made to replace the STII signal sequence with the lamb signal sequence, improving product yield.

Step 2: pAPlamB

Figure 9:
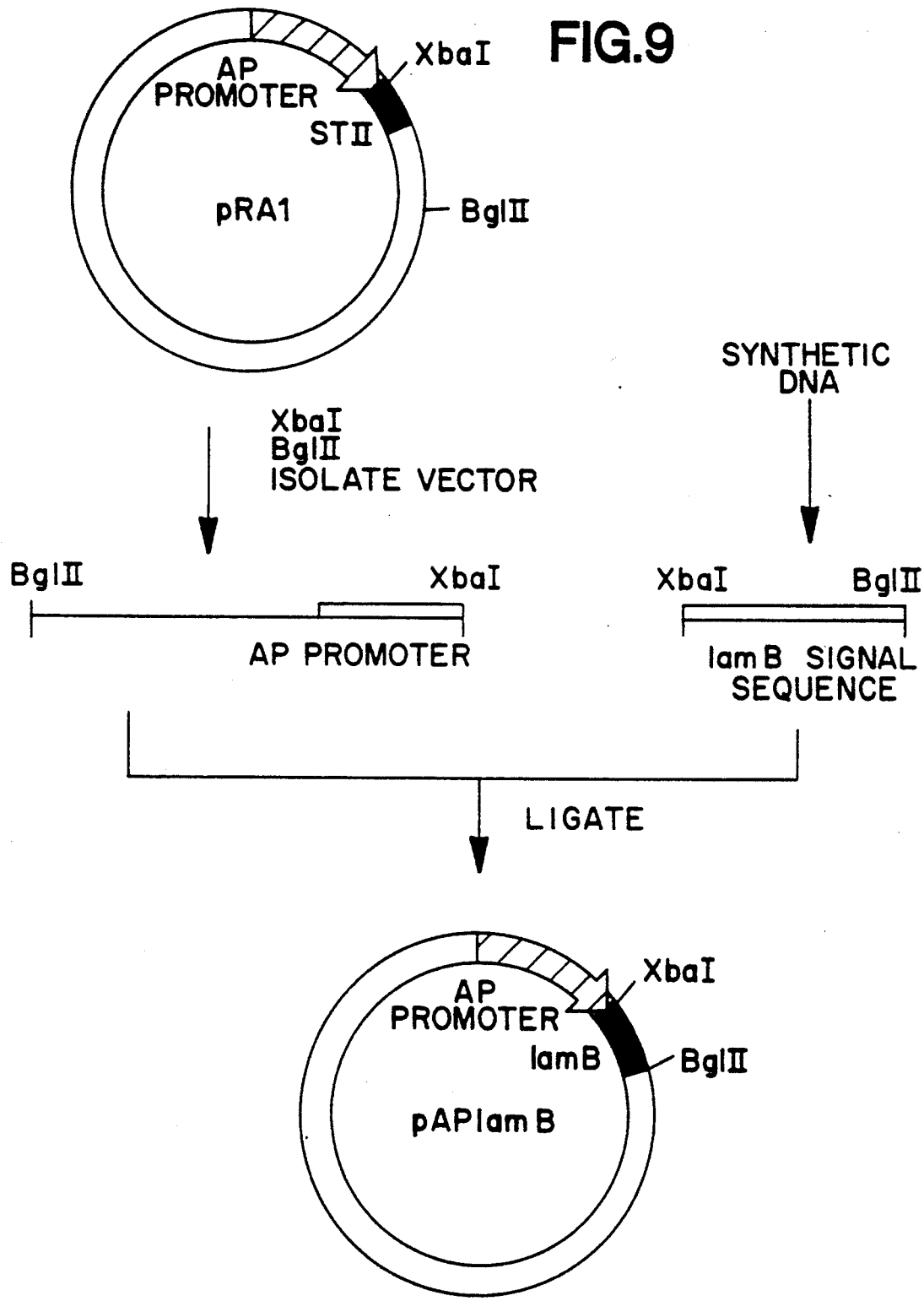
FIG. 9 depicts the construction of pAPlamB, another intermediate plasmid in preparing pLS32Tsc and in preparing an additional intermediate plasmid, pLamBIGF.

The plasmid pAPlamB was constructed as shown in FIG. 9 by ligating together two DNA fragments, and results in the placement of the lamb signal coding sequence downstream of the AP promoter and the trp Shine-Dalgarno sequence. Included in the ligation was the vector PRA1 in which the small XbaI-B-qIII fragment had been removed. This plasmid is a derivative of phGH1 [Chang et al., *Gene*, 55: 189-196 (1987)], which latter plasmid contains the AP promoter, the STII signal, and DNA encoding hGH. pRA1 differs from phGH1 in that it contains DNA encoding relaxin A chain (the sequence of which is described in U.S. Pat. No. 4,758,516) rather than hGH and it contains a convenient BglII restriction site downstream of the promoter and ribosome binding site. The second piece in the ligation was a 80-bp synthetic DNA duplex with the following sequence, which, encodes the lass signal sequence, described by Clement and Rofnung, *Cell*, 27: 507-514 (1981):

```
                   GTCGCAGCGGGCGTAATGTCTGCTCAGGCCATGGCCA - 3'
                   GCGTCGCCCGCATTACAGACGAGTCCGGTACCGGTCTAG - 5'
```

(SEQ. ID NOS. 19 and 20, respectively)

Step 3: pLS32lamB

Figure 10:
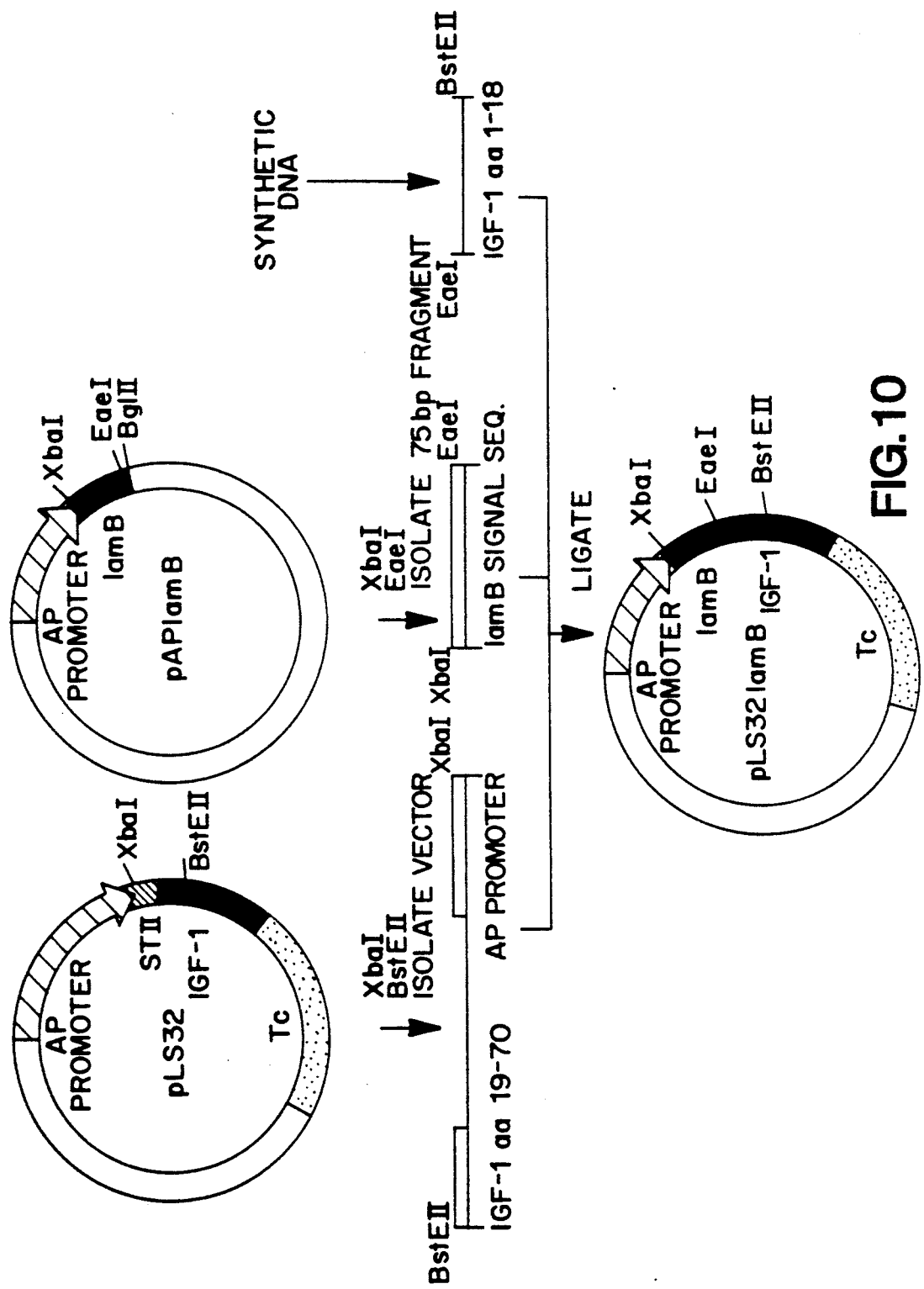
FIG. 10 depicts the construction of pLS32lamB, still another intermediate plasmid in the construction of pLS32Tsc.

The plasmid pLS32lamB results in the fusion of the lamb signal sequence to the IGF-I coding region and was constructed as shown in FIG. 10 by the ligation of three DNA fragments. The first of these was the vector pLS32 in which the small XbaI-BstEII fragment had been removed. The second was a 75-bp XbaI-EaeI fragment from pAPlamB encoding the lamb signal sequence. The third was a 55-bp synthetic DNA duplex encoding the first 18 amino acids of mature IGF-I, and having the following sequence:

```
5' - GGCCGGTCCCGAAACTCTGTGCGGTGCTGAACTGGTTGACGCTCTGCAGTTTGTTTGCG - 3'
3' - CCAGGGCTTTGAGACACGCCACGACTTGACAACTGCGAGACGTCAAACAAACGCACACTG - 5'
```

(SEQ. ID NOS. 21 and 22, respectively)

The following steps introduce into the plasmid the transcriptional terminator. These plasmid changes resulted in an improved product yield.

Step 4: pLS33lamB

Figure 11:
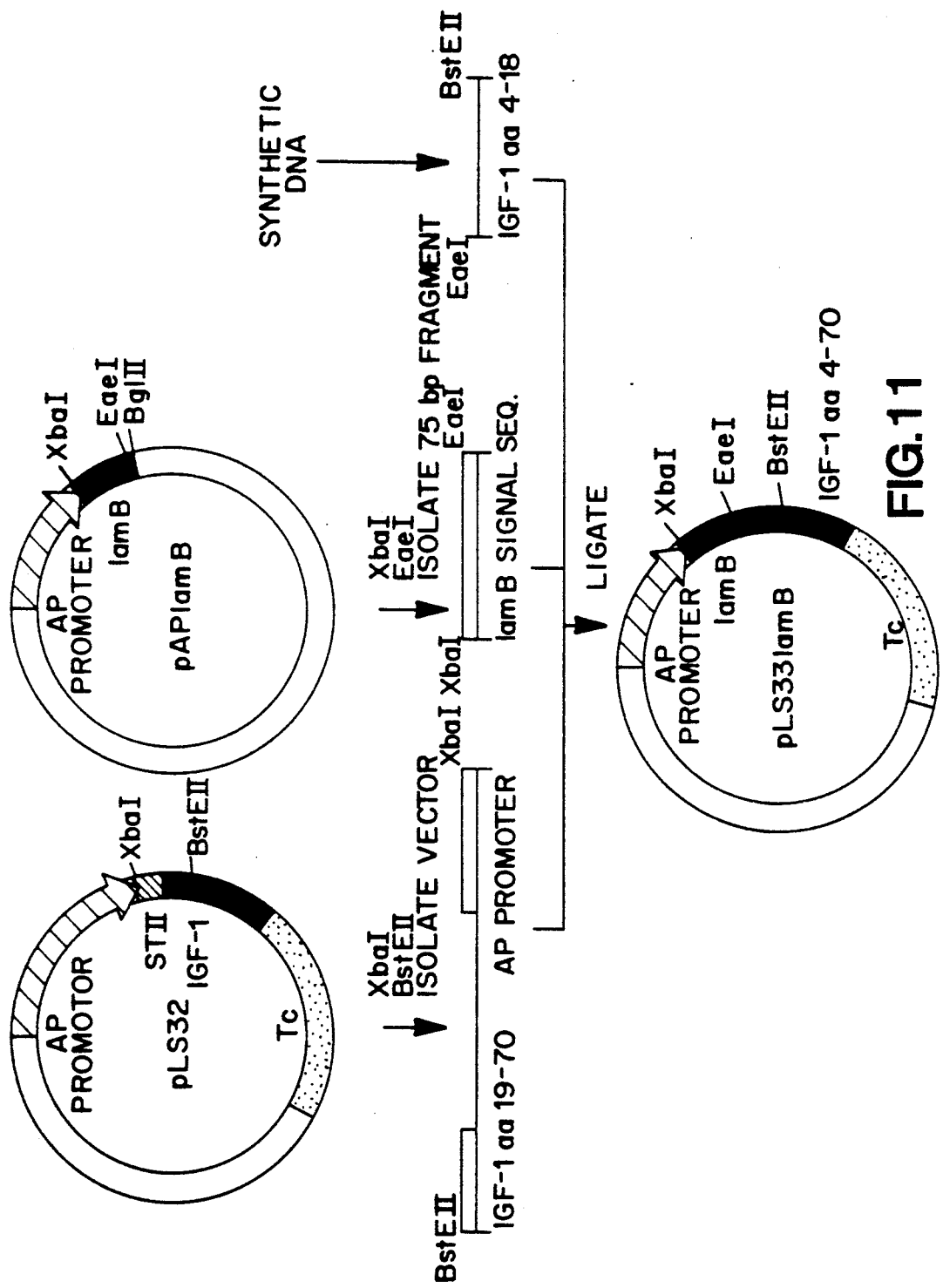
FIG. 11 depicts the construction of pLS33lamB, another intermediate plasmid in the preparation of pLS32Tsc.

The plasmid pLS33lamB, is an intermediate in the preparation of pLS32Tsc and was constructed as shown in FIG. 11 by ligating together three DNA fragments. The first of these was the vector pLS32 in which the small XbaI-BstEII fragment had been removed. The second was a 75-bp XbaI-EaeI fragment from pAPlamB encoding the lamB signal sequence. The third was a 46-bp synthetic DNA duplex with the following sequence:

```
5'- GGCCACTCTGTGCGGTGCTGAACTGGTTGACGCTCTGCAGTTTGTTTGCG - 3'
3'- TGAGACACGCCACGACTTGACCAACTGCGAGACGTCAAACAAACGCCACTG - 5'
```

(SEQ. ID NOS. 23 and 24, respectively)

The above sequence encodes amino acids 4-18 of mature IGF-I.

Step 5: pLS33Tsc

Figure 12:
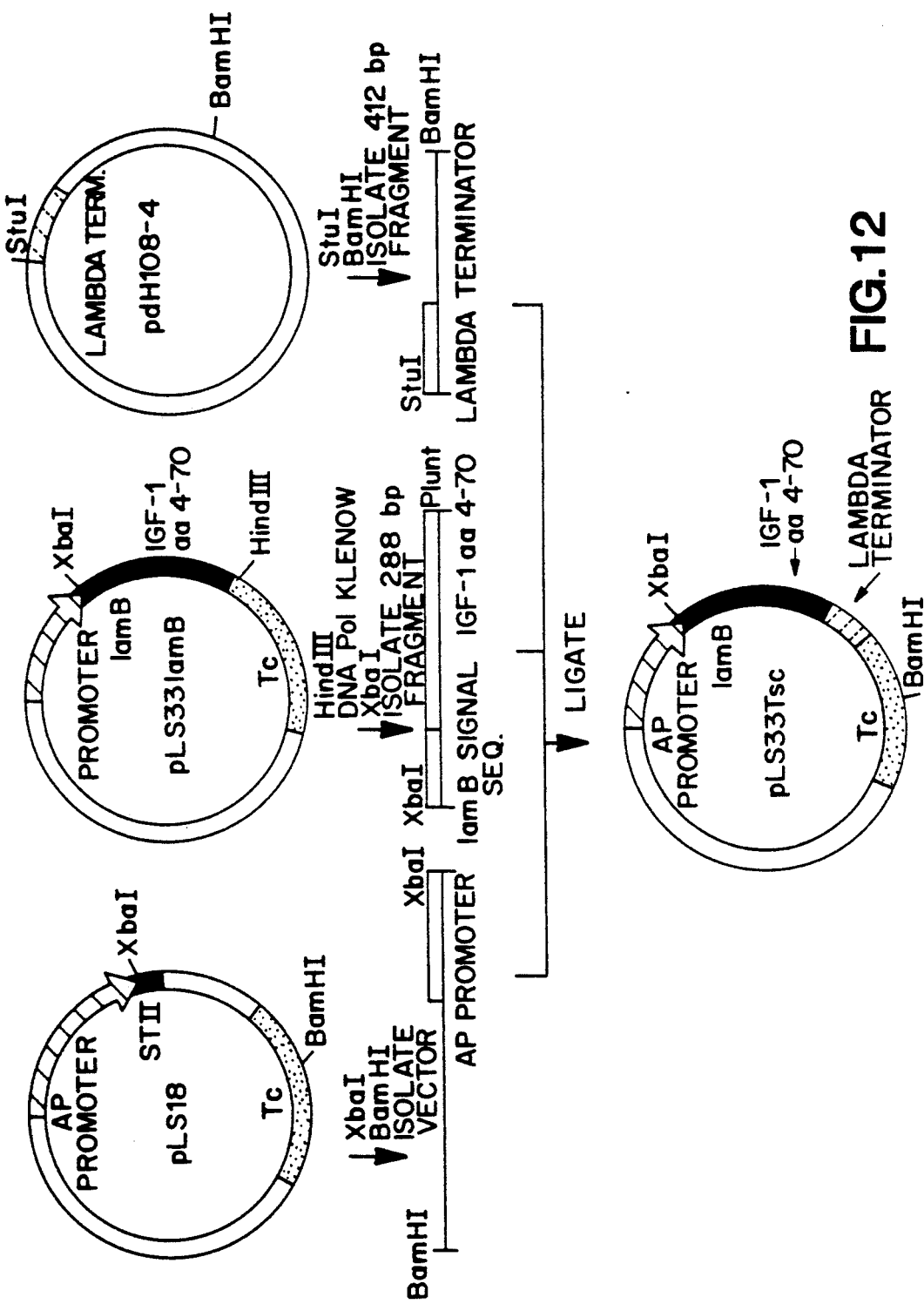
FIG. 12 depicts the construction of pLS33Tsc, another intermediate in the preparation of pLS32Tsc and pBKIGF-2.

The plasmid pLS33Tsc results in the placement of the lambda $t_o$ transcriptional terminator immediately downstream of the IGF-I coding sequence. Three DNA fragments were ligated together as shown in FIG. 12 to construct this plasmid. The first piece was the vector pLS18 in which the small ZbaI-BamHI fragment had been removed. pLS18 is a derivative of phGH1 [Chang et al., supra] that contains DNA encoding human DNaBe (as disclosed in WO 90/07572 published Jul. 12, 1990) rather than hGH. phGH1 could be used to generate the same fragment. The fragment contains from the BamHI site to the 3' end of the tetracycline gene, thereby missing about 300-bp at the 5' end of the gene.

The second part of the ligation was a 288-bp XbaI-HindIII fragment from pLS33lamB in which the HindIII restriction site had been blunted by treatment with DNA polymerase I (Klenow).

The third part of the ligation was a 412-bp StuI-BamHI fragment from the plasmid pdH108-4. This fragment contains the lambda $t_o$ transcriptional terminator [Scholtissek and Grosse, Nuc. Acids Res., 15: 3185 (1987)] and base pairs 2-375 of pBR322 [Sutcliffe, supra], wherein the base pairs 2-375 are downstream or 3' of the transcriptional terminator. The sequence of the terminator region of this fragment is as follows:

```
5' - CCTAACGCTCGGTTGCCGCCGGGCGTTTTTTATTGTTAA - 3'
3' - GGATTGCGAGCCAACGGCGGCCCGCAAAAAATAACAATT - 5'
```

(SEQ. ID NOS. 25 and 26, respectively)

Step 6: DLS32Tsc

Figure 13:
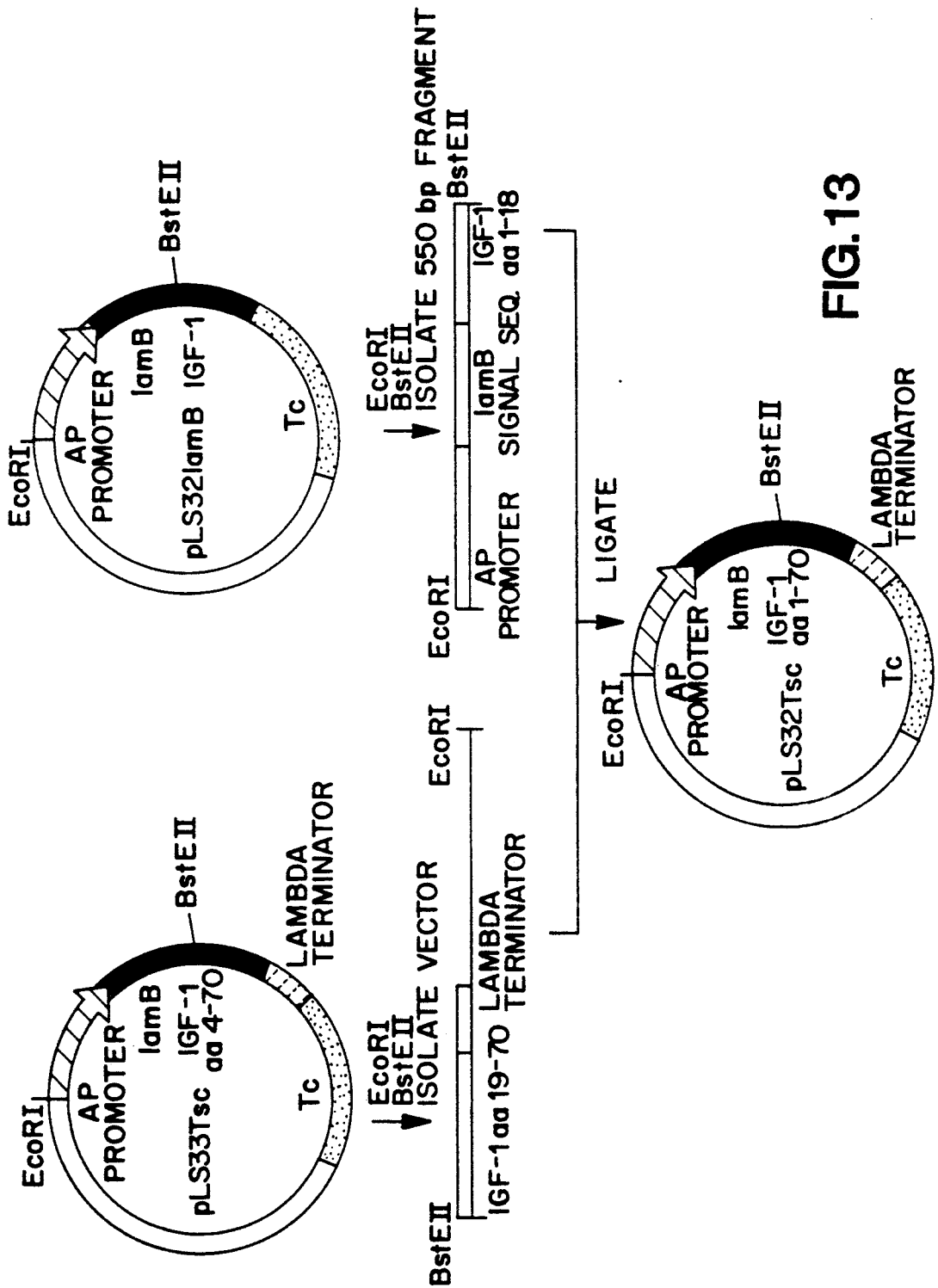
FIG. 13 depicts the construction of pLS32Tsc from pLS33Tsc and pLS32lamB.

The final plasmid pLS32Tsc was constructed as shown in FIG. 13 by ligating together two DNA fragments. The first of these was the vector pLS33Tsc from which the small EcoRI-BstEII fragment had been removed. The second was a 550-bp EcoRI-BstEII fragment from pLS32lamB containing the AP promoter, trp Shine-Dalgarno sequence, and the coding sequence for the lamB signal sequence fused to the first 18 amino acids of IGF-I. The resulting plasmid was analyzed by restriction endonuclease digestion. The entire promoter and coding sequence of pLS32Tsc was verified by DNA sequencing, with the sequence being given in FIG. 14 (SEQ. ID NO. 27). Also provide in FIG. 14 is the amino acid sequence (SEQ. ID NO. 28) encoded by the lamB signal sequence and IGF-I DNA in pLS32Tsc.

Step B: pLBIGFTsc

Step 1: pLamBIGF

Figure 15:
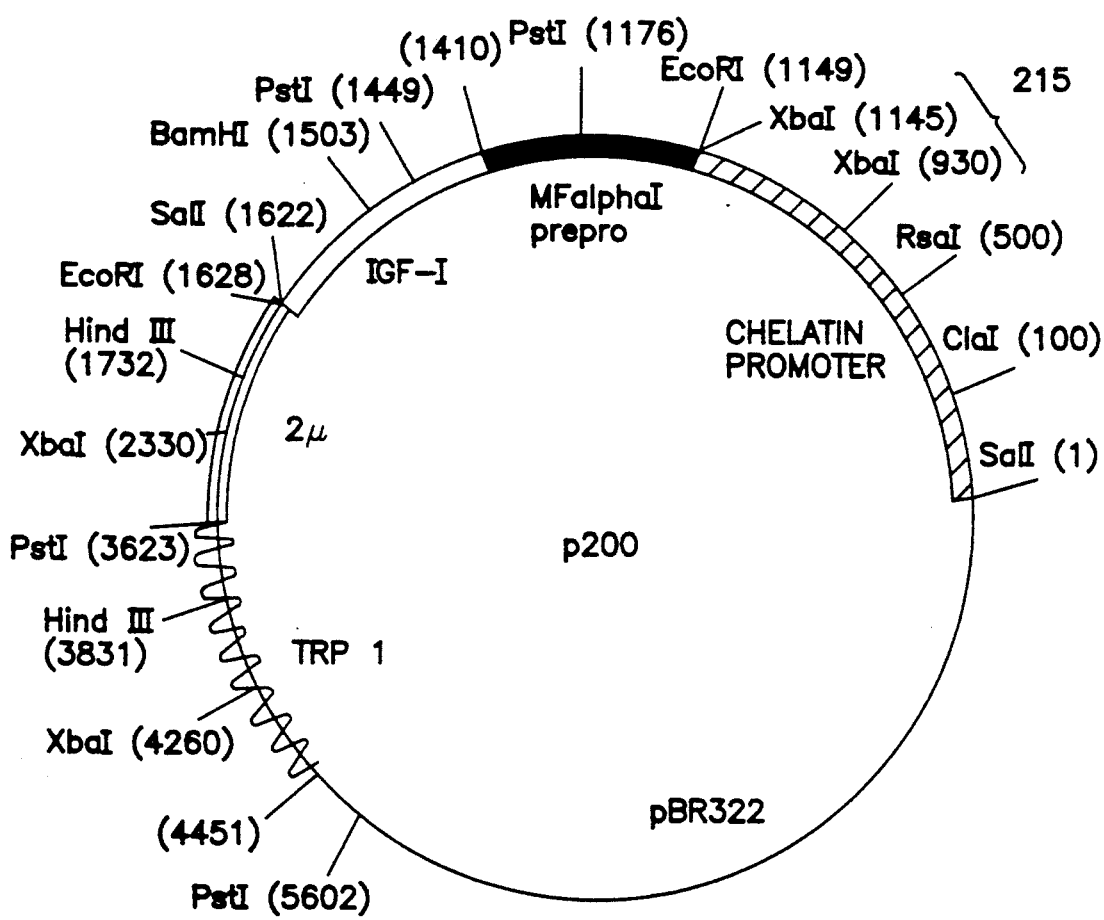
FIG. 15 shows a restriction map for plasmid p200, used to produce pLamBIGF, an intermediate plasmid in the production of pLBIGFTsc, used to prepare pBKIGF-2.

For the first part of the ligation, the EcoRI-PstI vector fragment from pBR322 was isolated. For the second part of the ligation, a PstI-NcoI 1244-bp fragment was isolated from pAPLamB. For the third part of the ligation, the HaeII-EcoRI 196-bp fragment containing the IGF-I gene except the initial 5' end was isolated from plasmid p200. p200 is a pBR322-derived plasmid having, in the 5' to 3' order, the chelatin promoter, the MF alpha I prepro signal sequence, DNA encoding mature IGF-I, and the 2-micron terminator. It contains the ColE1 origin of replication for bacteria and the 2-micron origin for yeast. A restriction enzyme plasmid diagram of p200 is provided in FIG. 15. The nucleotide sequence (SEQ. ID NO. 29) of the EcoRI (starting at position 1149) to EcoRI (starting at position 1628) fragment of p200 containing the MF alpha I prepro and IGF-I gene is provided in FIG. 16. The HaeII, PstI, BamHI, and SalI restriction sites that are also in the diagram in FIG. 15 are indicated in the sequence by underlining. A piece of synthetic DNA linking the signal sequence to the IGF-I gene (NcoI to HaeII) was prepared with the following sequence:

```
5'- CATG GCC GGT CCG GAA ACT CTG TGC GGC GC    (SEQ. ID NO. 30)
3'-      CGG CCA GGC CTT TGA GAC ACG C         (SEQ. ID NO. 31).
```

Figure 17:
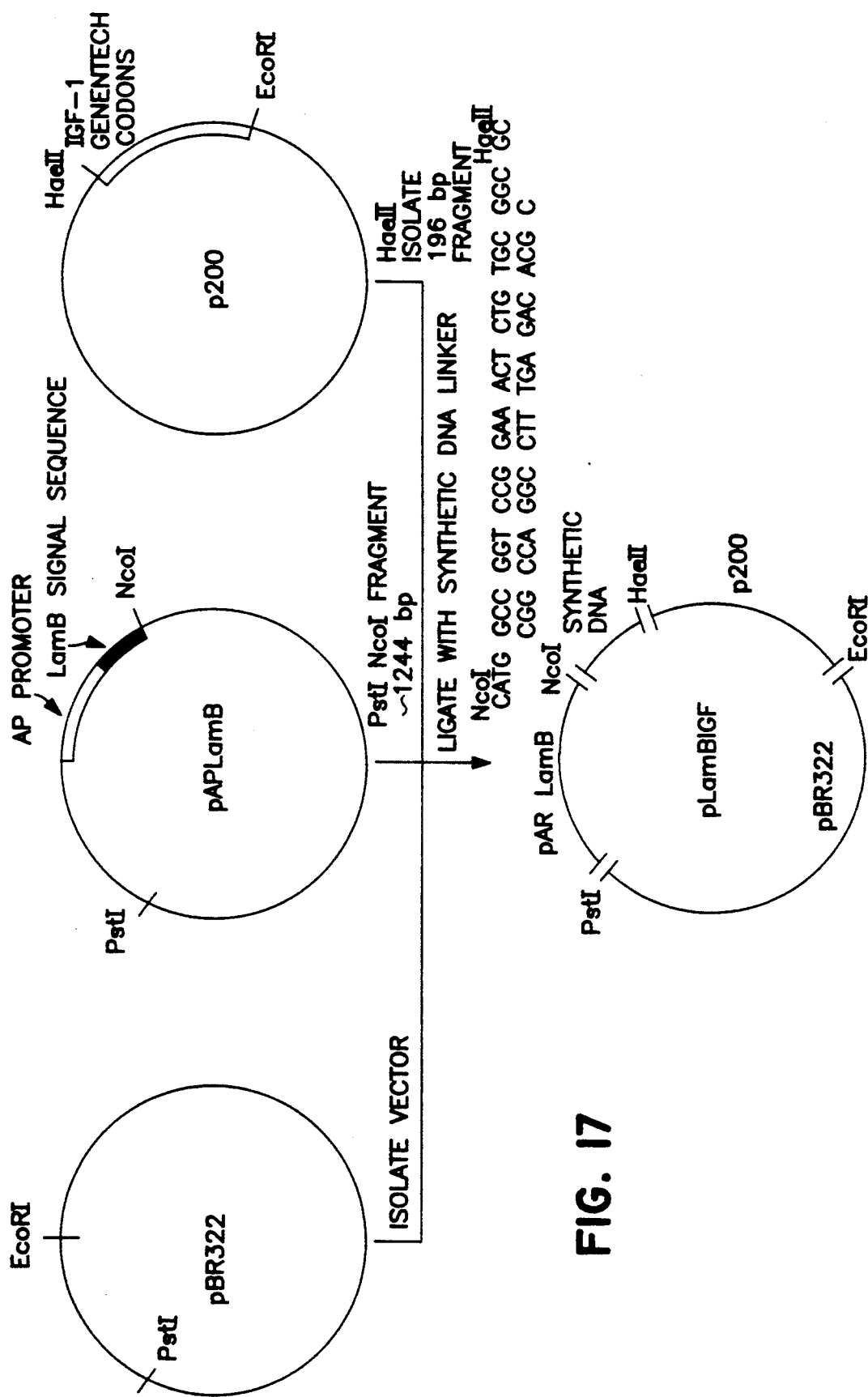
FIG. 17 depicts the construction of pLamBIGF from three plasmid fragments and a piece of synthetic DNA (SEQ. ID NO. 30 and SEQ. ID NO. 31).

The three plasmid fragments and the synthetic DNA were ligated together to form pLamBIGF, as shown in FIG. 17.

Step 2: pLBIGFTsc

Figure 18:
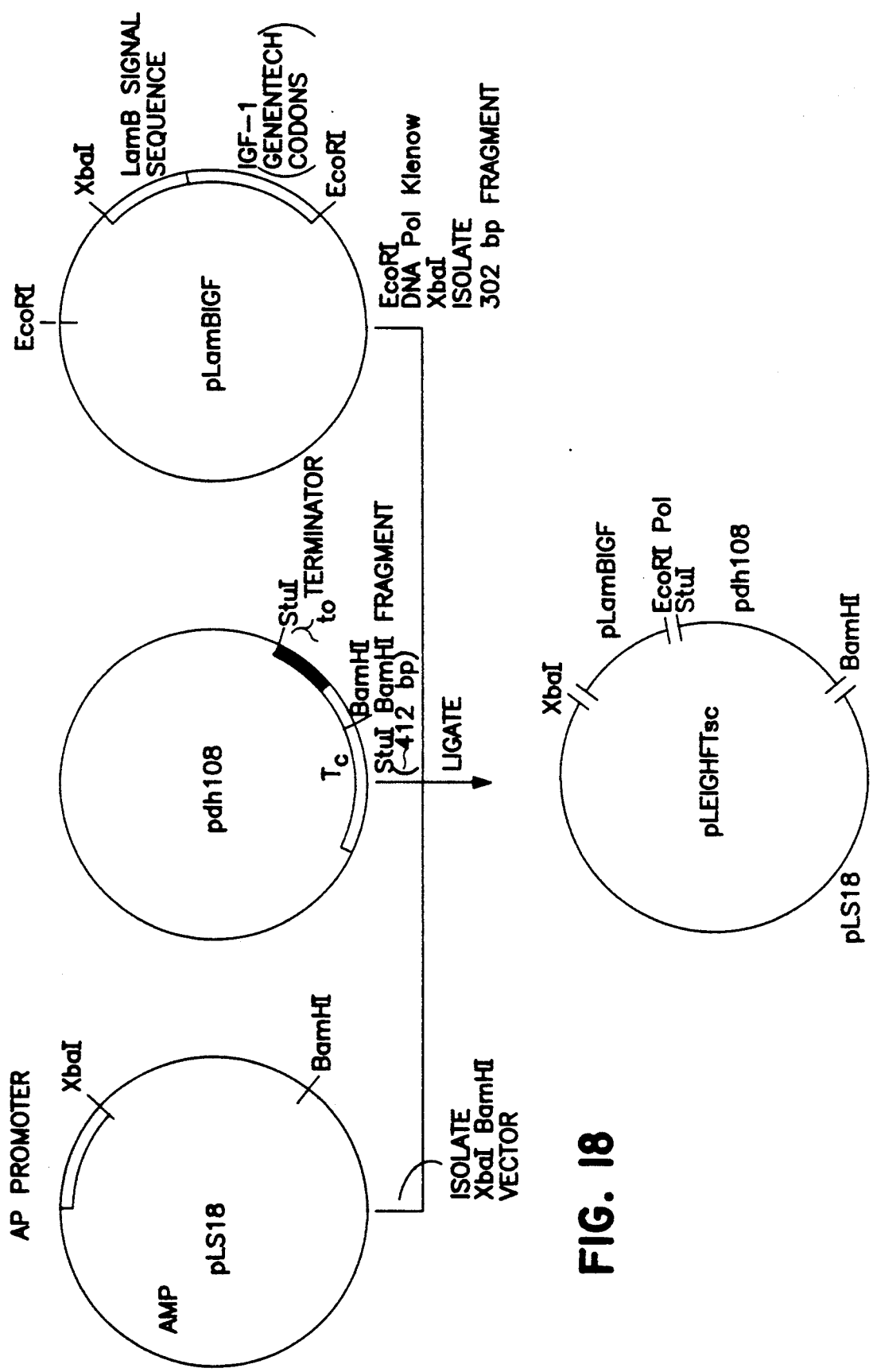
FIG. 18 depict the construction of the intermediate plasmid pLBIGFTsc from pLamBIGF.

The XbaI-BamHI vector fragment was isolated from pLS18 as the first ligation fragment. The second part of the ligation was a 412-bp StuI-BamHI fragment from the plasmid pdH108-4 described above. The third part of the ligation was prepared by an EcoRI digest of pLamBIGF, followed by treatment with DNA polymerase Klenow fragment, followed by a XbaI digest. The resultant 302-bp fragment was isolated. These three fragments were ligated to yield pLBIGFTsc, as shown in FIG. 18.

Step C: pRanTsc

Figure 19:
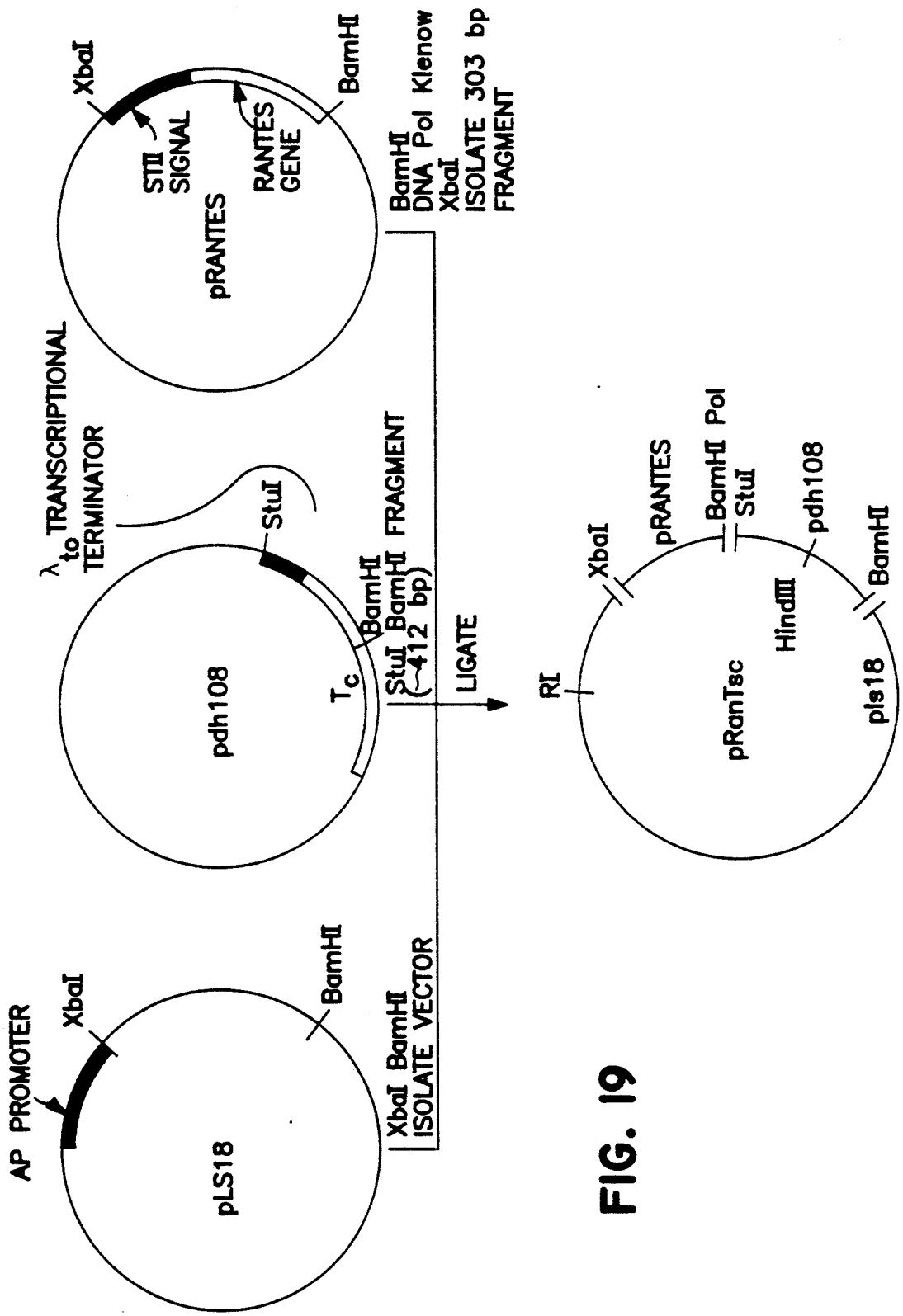
FIG. 19 depicts the construction of the intermediate plasmid pRanTsc used in the production of pBKIGF-2.

The XbaI-BamHI vector fragment from pLS18 was isolated as the first ligation fragment. The second part of the ligation was a 412-bp StuI-BamHI fragment from the plasmid pdH108-4 described above. The third part of the ligation was prepared from pRANTES. pRANTES is a pBR322-based plasmid containing a fragment of a XbaI linker followed by the STII signal, followed by the CDNA encoding RANTES [as published by Schall et al., J. Immunol., 141: 1018 (1988)], followed by the BamHI linker. The third fragment was prepared by digestion of pRANTES with BamHI, followed by treatment with DNA polymerase Klenow fragment, followed by a XbaI digest. The resultant 303-bp fragment was isolated. These three fragments were ligated to yield pRanTsc, as shown in FIG. 19.

Step D: DBKIGF-2

Figure 20:
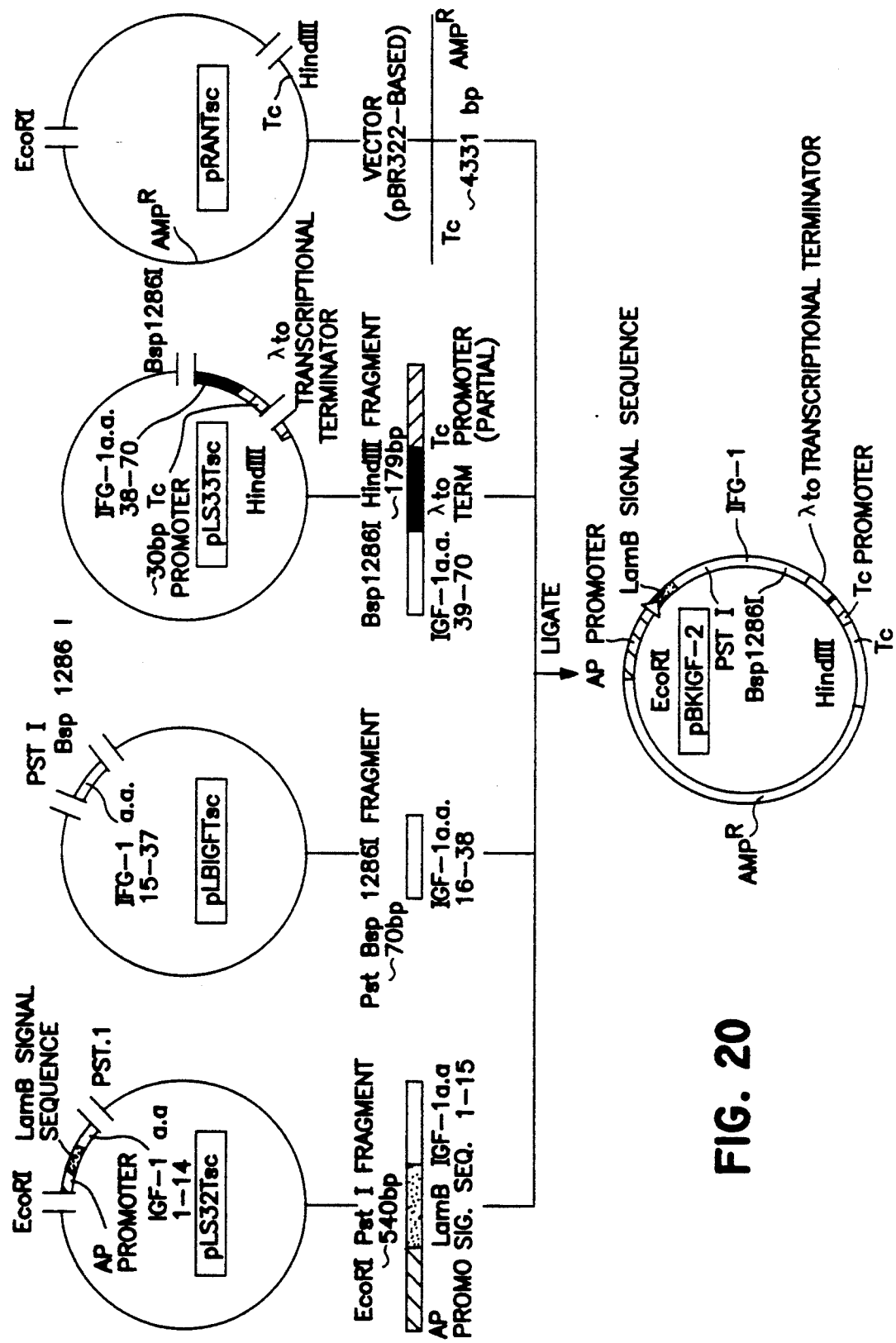
FIG. 20 depicts the construction of pBKIGF-2 from pLS32Tsc, pLBIGFTsc, pLS33Tsc, and pRanTsc.

As shown in FIG. 20, the EcoRI-PstI 540-bp fragment containing the alkaline phosphatase promoter, the lamB signal sequence, and DNA encoding the first 15 amino acids of IGF-I was excised from pLS32Tsc. The Pst-Bsp1286I fragment (~70 bp) containing DNA encoding amino acids 16-38 of IGF-I was excised from pLBIGFTsc. The Bsp1286I-HindIII (~179-bp) fragment containing DNA encoding amino acids 39-70 of IGF-I, the lambda terminator, and the 5'-portion (~30 bp) of the Tc promoter was excised from pLS33Tsc. Finally, the EcoRI-HindIII ~4331-bp vector fragment (pBR322-based) was excised from pRanTsc. These four fragments were ligated to give pBKIGF-2, which contains the AP promoter, the lamb signal sequence, the DNA encoding the entire IGF-I protein, the transcriptional terminator, the Tc promoter, and the tetracycline and ampicillin resistance markers.

Culturing

The five transformed strains were evaluated in shake-flask cultures as follows. Approximately 0.3 ml of an overnight culture grown in LB medium plus 10 μg/ml tetracycline was inoculated into 20 ml of low-phosphate medium so that the initial cell density was 0.05 (A550) and the phosphate carryover was less than 0.04 MM. The low-phosphate medium contained required mineral salts, and 1.1% Hycase SF plus 0.064 yeast extract. The total initial phosphate concentration was estimated to be 0.2 mM. The composition of the medium was as follows: 10 μg/ml tetracycline, 1.5 g/l glucose, 1.6 mM MgSO4, 20 mM NH4Cl, 50 mM KCl, 20 mM NaCl, and 120 mm triethanol amine, pH 7.4. For the cultures with higher initial phosphate concentrations, inorganic phosphate was added to achieve the indicated initial total phosphate concentration.

The cultures were shaken at 37° C. in 125-ml baffled flasks for 24 hours, at which time they had reached their maximal cell density. The cell density (A550) was measured and cell samples were taken for analysis of total cell-associated IGF-I concentration. Cells were isolated by centrifugation and the cell-associated IGF-I was solubilized and extracted with 6M urea, 10 mM DTT, 5 mM EDTA, and 50 mM Tris buffer, pH 8.0. The samples were then centrifuged and filtered before HPLC analysis. HPLC analysis was conducted with two Polymer Labs PLRP-S columns in series at 50° C. using 0.1% trifluoroacetic acid and an acetonitrile concentration gradient between 32% and 45% with a mobile-phase flow rate of 1.5 ml/min.

Results

Figure 21:
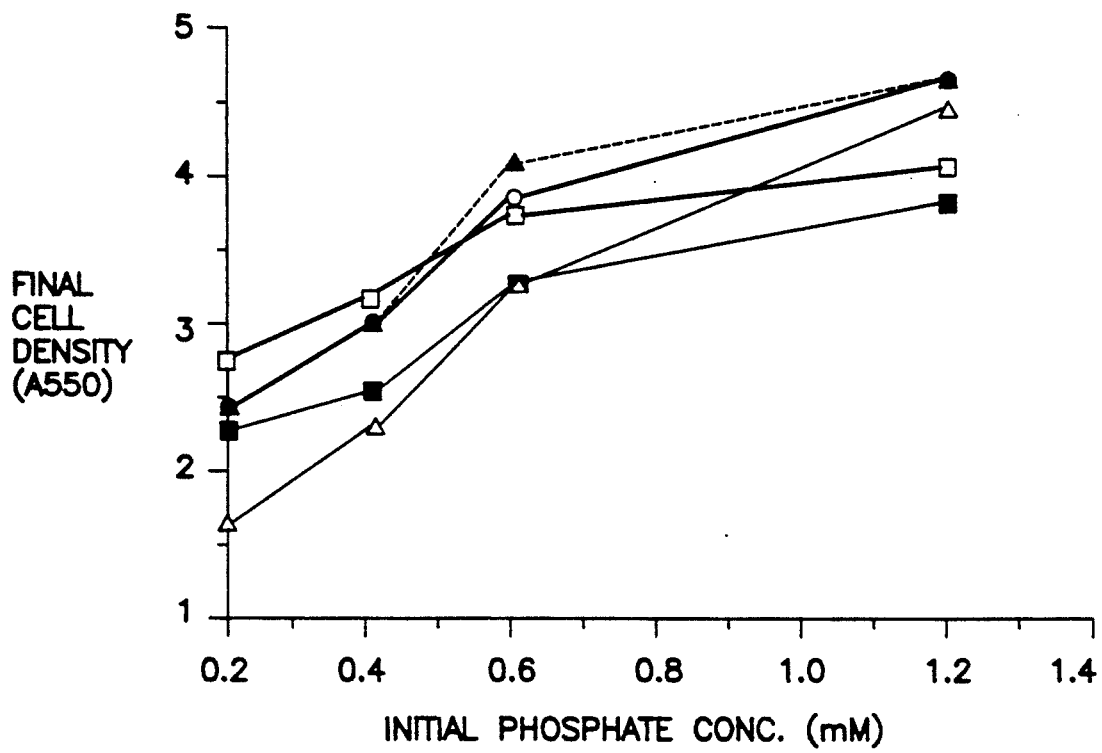
FIG. 21 shows the final cell density obtained in shake flask cultures for various *E. coli* strains transformed with pBKIGF-2 as a function of the initial phosphate concentration in the medium. The open squares are wild-type strain 9E4 (pstS+), the solid squares are mutant strain 39B4 (T10M), the open triangles are mutant strain 39B5 (T10Y), the open circles are mutant strain 39B6 (T141H), and the solid are mutant strain 39B7(D56S).
Figure 22:
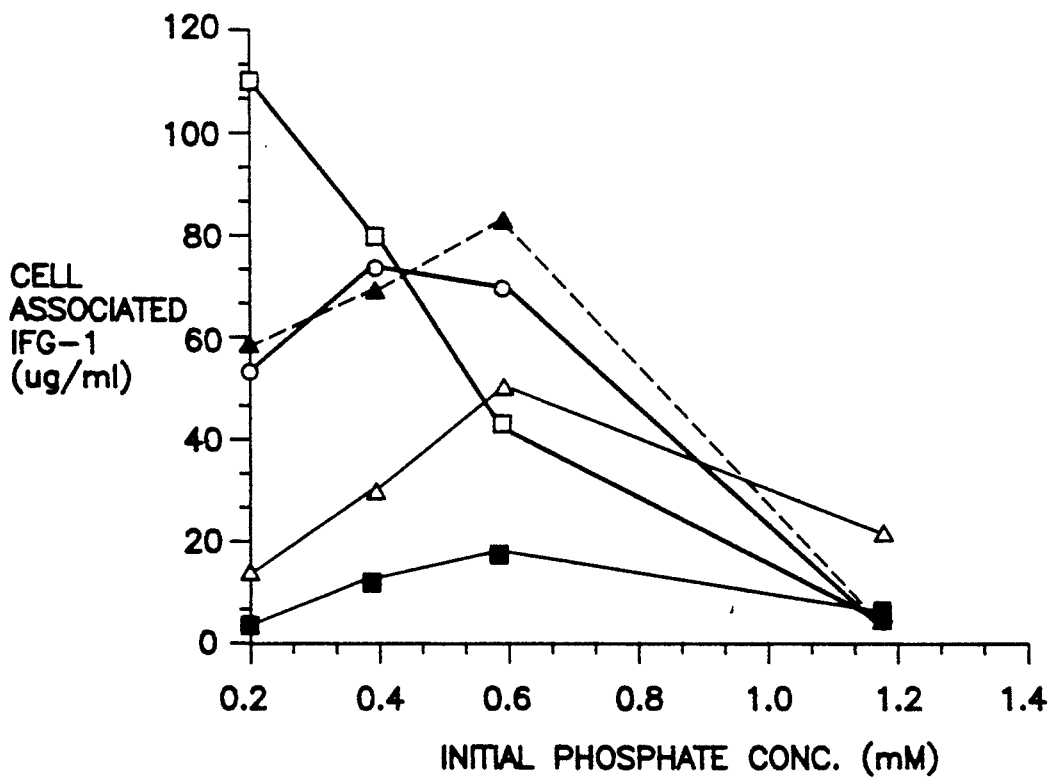
FIG. 22 illustrates the concentration of cell-associated IGF-I determined by HPLC as a function of initial phosphate concentration. The symbols are as defined in the legend for FIG. 21.

FIG. 21 shows the final cell density obtained for the various organisms as a function of the initial phosphate concentration in the medium. As might be expected, the organisms with the mutated PstS proteins did not grow as well on media with low-phosphate concentrations, although all of the organisms reached approximately the same cell density at high-phosphate concentration. FIG. 22 presents the HPLC results for cell-associated IGF-I concentrations. These results also indicate that the lowered affinity of the PstS protein for phosphate has allowed more IGF-I accumulation at the higher phosphate concentrations (0.6 and 1.2 mM initial PO4) than can be produced by the organism with the wild-type pstS protein. The best producer for those studied in this experiment was T10Y PstS.

EXAMPLE III

High-Cell-Density Fermentations with Mutant Strains

To test utility of the pstS mutants in a practical setting, fermentation experiments were conducted. The objective was to test for the effect of lowered PstS affinity for phosphate on the production of the heterologous product, IGF-I, in an industrially relevant high-cell-density fermentation. It is expected that maximal utility would be realized by controlling a phosphate feed stream based on on-line measurements of phosphate concentration in the growth medium. However, a more easily implemented mode for the invention would be to use a constant, but higher rate of phosphate feeding with the pstS mutants than with the wild-type organism. This type of experiment is described in the following paragraphs.

The cell strains employed in Example II for the shake-flask experiments were transformed with pBKIGF-2 by standard transformation techniques. Transformants were selected and purified on LB plates containing 20 mg/L tetracycline. This medium had the following composition: 10 g/L Bacto-Tryptone, 5 g/L yeast extract, 10 g/L sodium chloride, and 20 mg/L tetracycline-HCl.

One transformed colony from each cell type was used to inoculate sterile LB broth containing 20 mg/L tetracycline. The flask cultures were incubated at 35°-39° C. until the optical density at 550 nm reached approximately 1.0. Sterile DMSO was added to the cultures to give a final concentration of DMSO of 10% (v/v). Aliquots of 1-2 ml were dispensed into sterile vials and stored at −60° C. or below.

The fermentor inocula for producing rhIGF-I were prepared by inoculating 1 ml of each frozen 1-OD (A550) culture into 500 ml of LB medium containing 5 μg/ml tetracycline. These cultures were incubated for 8 hours in a shaken 2-liter baffled flask at 37° C. until the cultures reached approximately 3OD. The shake flask was then used to inoculate a 10-liter fermentor containing 6 liters of culture medium composed as follows:

| Ingredient | Quantity/Liter |
| --- | --- |
| glucose* | 2.5 g |
| ammonium sulfate | 2-6 g |
| ammonium hydroxide | as required to control pH 7.1 to 7.5 |
| sodium phosphate, monobasic dihydrate | ** |
| potassium phosphate, dibasic | ** |
| sodium citrate, dihydrate | 0.5-1.5 g |
| potassium chloride | 1-2 g |
| 25% Pluronic Polyol L61 | 0.2 ml initially and as needed to control foaming |
| magnesium sulfate, heptahydrate | 1-3 g |
| tetracycline HCl | 8.3 mg |
| yeast extract*** | 12.5 g |
| NZ amine AS*** | 12.5 g |
| isoleucine | 0-10 g |
| ferric chloride, heptahydrate | 10-30 mg |
| zinc sulfate, heptahydrate | 2-5 mg |
| cobalt chloride, hexahydrate | 2-5 mg |
| sodium molybdate, dihydrate | 2-5 mg |
| cupric sulfate, pentahydrate | 2-5 mg |
| boric acid | 0.5-2 mg |
| manganese sulfate, monohydrate | 1-3 mg |

*This amount of glucose was added to the culture initially. A remaining amount was fed to the culture over the course of the fermentation as described below.
**The amount of inorganic phosphate was an amount sufficient such that the total batched phosphate was approximately 293 mmoles.
***Yeast extract and NZ amine AS can be added initially and/or fed throughout the fermentation.

The fermentation process was performed at 37° C. with vigorous agitation and aeration at pH 7.3, the pH being controlled using ammonium hydroxide additions. The agitation rate was set at 650-1000 rpm and the aeration rate at 0.7–1.5 volumes of air per volume of culture per minute. After the initial glucose was exhausted, a sterile 50% glucose solution was fed to maintain the culture at near its maximal growth rate during the initial part of the fermentation at a rate fast enough to allow rapid growth, but not so rapid as to cause the dissolved oxygen level to fall below 30% of air saturation levels during the latter portion of the fermentation (when significant cell mass has accumulated).

At approximately 40 OD (6–9 hours after inoculation), a complex nitrogen feed was started. Three different feeds were used and were termed 1X, 2X, and 4X in rough proportion to the amount of phosphate delivered. The following table describes the three feeds:

| Feed | Conc. of Yeast Extract (%) | Conc. of NZ Amine AS (%) | Extra PO4 (mM) | Feed Rate (ml/min.) | Rate of PO4 Addition (μmole/min) |
|---|---|---|---|---|---|
| 1X | 6.5 | 13.5 | 0 | 0.2 | 14 |
| 2X | 6.0 | 12.3 | 66 | 0.2 | 27 |
| 3X | 5.1 | 10.5 | 170 | 0.25 | 57 |

Approximately 12 hours after inoculation, the phosphate in the medium was exhausted and production of IGF-I was induced. The fermentations were continued until 40 hours after inoculation, with samples taken every two hours to assess total accumulated IGF-I. Whole broth samples were extracted with 6M guanidine HCl and 100 mM DTT in a 50 mM Tris buffer, pH 9.0. The extracted IGF-I was assayed by HPLC using a Bakerbond reverse-phase column with a 34–35% acetonitrile gradient in 0.1% trifluoroacetic acid at 2 ml/min. and 50° C.

Figure 23:
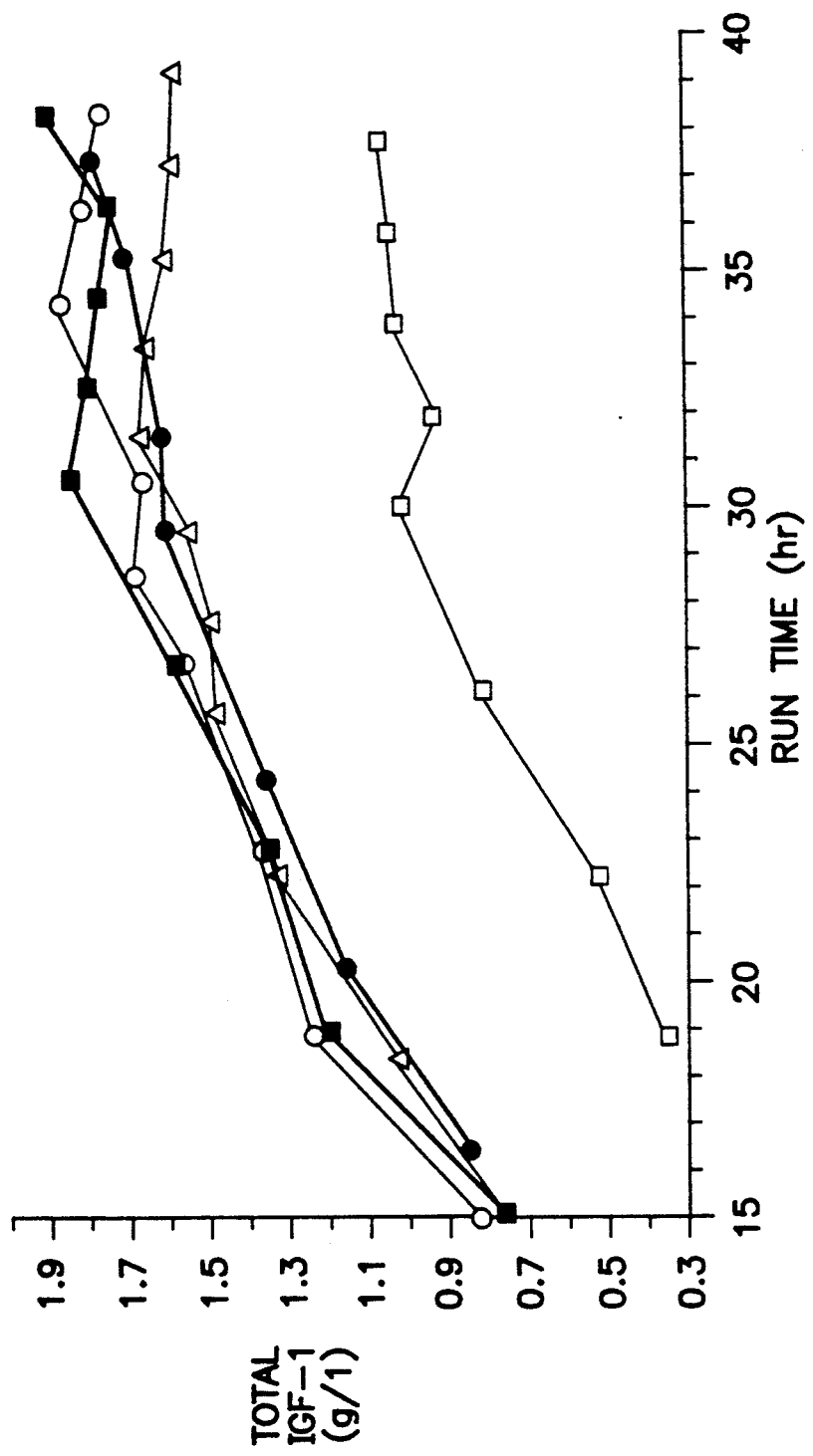
FIG. 23 illustrates the total IGF-I concentration as a function of high-cell-density fermentation run time for four of the pstS mutants versus the wild-type host, all transformed with pBKIGF-2. The open squares are wild-type strain 9E4 (pstS+), the solid diamonds are mutant strain 39B4(T10M), the open circles are mutant strain 39B5 (T10Y), the open triangles are mutant strain 39B6(T141H), and the solid squares are mutant strain 39B7(D56S).

FIG. 23 presents results obtained with the 2X feed for four of the pstS mutants versus the wild-type host. There was a significant benefit in total IGF-I accumulation with all of the mutants investigated.

Figure 24:
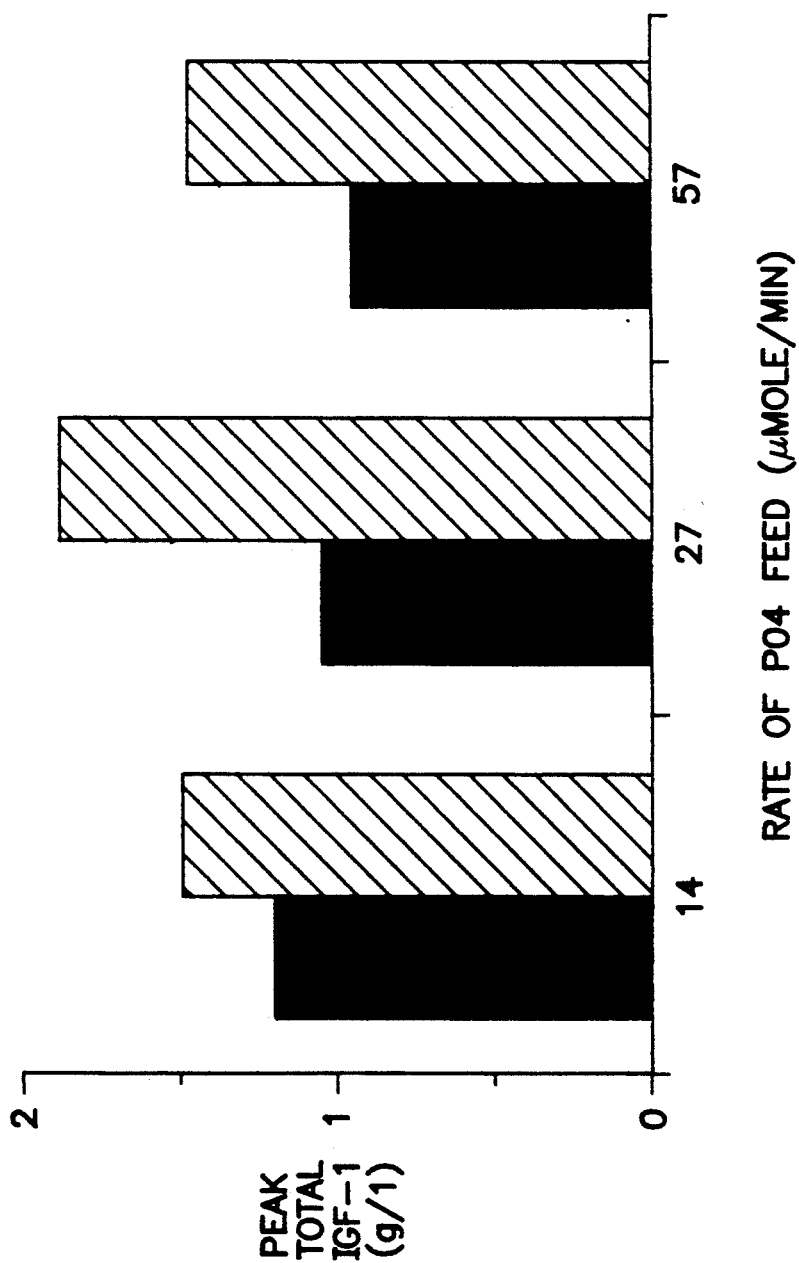
FIG. 24 shows the effect of increasing rates of phosphate feed on IGF-I production by host organisms having wild-type (solid bars] and mutated [diagonal bars, 39B7(D56S)] pstS proteins.

For further characterization of the performance of the mutated organisms, the transformed 39B7 host with a D56S pstS mutation was evaluated versus the host with the wild-type pstS protein for peak total IGF-I at three different rates of phosphate feed, namely 14, 27, and 57 μmole/min. FIG. 24 shows that at all three phosphate feed rates, 39B7/pBKIGF-2 produced more product. For the wild-type host, higher phosphate feed rates reduced IGF-I accumulation. For the mutant, the highest IGF-I accumulation occurred with the intermediate feed rate, consistent with control effected by the PstS protein with a lower affinity for phosphate. At this feed rate, IGF-I accumulation was 78% higher for the mutant 39B7 than that for the wild-type 9E4 and was 58% higher than the IGF-I accumulation obtained for the wild-type host at its optimal phosphate feed rate, 14 μmole/min.

In summary, the periplasmic phosphate-binding protein PstS is a component of the active transport system for phosphate in *E. coli* that is involved in regulating over twenty genes referred to as the pho regulon, which are induced upon phosphate limitation. The PstSCAB and PhoU proteins act as negative regulators of these genes in conditions of high phosphate.

The role of phosphate binding by PstS in the regulation of the pho regulon was determined by assaying alkaline phosphatase (PhoA) activity in strains containing mutations in the phosphate-binding pocket of PstS that were grown on a range of phosphate concentrations. The crystal structure of PstS implicates the side chains of six residues in phosphate binding. The importance of these residues was initially determined by alanine-scanning mutagenesis. Expression of PhoA was relatively unchanged, so these residues were then singly randomized to all possible substitutions and the mutant pools were screened for increased PhoA activity after growth in high-phosphate media. Mutations in pstS were isolated that lead to increased expression of PhoA at higher phosphate concentrations. These mutations also allow higher expression and accumulation of heterologous products, e.g., IGF-I, in high-cell-density fermentations of industrial importance.

What is claimed is:

1. An isolated nucleic acid molecule encoding an *E. coli* PstS variant selected from the group consisting of T10F PstS, T10L PstS, T10M PstS, T10Y PstS, T10A PstS, T10C PstS, TLOG PstS, D56V PstS, D56A PstS, D56L PstS, D56S PstS, S139T PstS, S139P PstS, S139L PstS, and T141H PstS.

2. The nucleic acid molecule of claim 1 that encodes T10M PstS, T10Y PstS, D56S PstS, or T141H PstS.

3. *E. coli* host cells comprising the nucleic acid molecule of claim 1 under the transcriptional control of the wild-type *E. coli* pstS gene promoter.

4. The host cells of claim 3 wherein the nucleic acid molecule is integrated into the chromosome thereof.

5. The host cells of claim 3 further comprising a nucleic acid molecule encoding a polypeptide of interest under the transcriptional control of the alkaline phosphatase promoter.

6. A method for producing a polypeptide of interest comprising culturing Enterobacteriaceae cells that lack their native pstS gene and comprise a nucleic acid molecule encoding a PstS variant having an amino acid variation within the phosphate-binding region of the corresponding native PstS, which nucleic acid molecule is under the transcriptional control of the wild-type pstS gene promoter, and which bacterial cells also comprise a nucleic acid molecule encoding the polypeptide of interest under the transcriptional control of the alkaline phosphatase promoter, wherein the culturing takes place in a culture medium with a concentration of inorganic phosphate in the medium that during all phases of cell growth is above the level at which the cells are starved for phosphate and takes place under conditions that allow expression of the nucleic acid encoding the polypeptide of interest.

7. The method of claim the concentration of inorganic phosphate at all phases of cell growth is about 0.55 mM and wherein the pstS variant is homologous to the native pstS gene in the host cells.

8. The method of claim 6 further comprising recovering the polypeptide from the cell culture.

9. The method of claim 8 wherein the polypeptide is recovered from the periplasm or culture medium.

10. The method of claim 6 wherein the polypeptide is alkaline phosphatase.

11. The method of claim 6 wherein the polypeptide is exogeneres to the host cells.

12. The method of claim 1 wherein the polypeptide is a mammalian polypeptide.

13. The method of claim 6 wherein the Enterobacteriaceae cells are *E. coli* cells.

14. The method of claim 6 wherein the amino acid variation in the nucleic acid molecule is an amino acid substitution.

15. The method of claim 14 wherein the Enterobacteriaceae cells are *E. coli* and a hydrophobic residue is substituted for threonine at position 10 of the phosphate-binding region of native *E. coli* PstS or a serine is substituted for aspartic acid at position 56 of the phosphate-binding region of native *E. coli* PstS.

16. The method of claim 14 wherein the nucleic acid molecule encoding a PstS variant encodes an *E. coli* PstS variant selected from the group consisting of T10F PstS, T10L PstS, T10M PstS, T10Y PstS, T10A PstS, T10C PstS, T10G PstS, S38F PstS, D56V PstS, D56A PstS, D56L PstS, D56S PstS, S139T PstS, S139P PstS, S139L PstS, and T141H PstS under the transcriptional control of the wild-type *E. coli* pstS gene promoter.

17. A method of controlling the rate of expression of a polypeptide in Enterobacteriaceae cells comprising culturing bacterial cells that lack their native pstS gene and that comprise a nucleic acid molecule encoding a PstS variant having an amino acid variation within the phosphate-binding region of the corresponding native PstS, which nucleic acid molecule is under the transcriptional control of the wild-type pstS gene promoter, and which bacterial cells also comprise a nucleic acid molecule encoding the polypeptide of interest under the transcriptional control of the alkaline phosphatase promoter, wherein the culturing is under conditions whereby the concentration of inorganic phosphate in the culture medium is controlled during the production phase of cell growth so that the polypeptide is produced under the transcriptional control of a partially induced alkaline phosphatase promoter.

18. The method of claim 17 wherein the concentration of inorganic phosphate is controlled by controlling the feed rate into the medium of inorganic phosphate or of a complex nitrogen source containing inorganic phosphate.

19. The method of claim 17 wherein the cells are *E. coli* cells and the amino acid variation in the nucleic acid molecule is an amino acid substitution.

20. The method of clan wherein the nucleic acid molecule encoding a PstS variant encodes an *E. coli* PstS variant selected from the group consisting of T10F PstS, T10L PstS, T10M PstS, T10Y PstS, T10A PstS, T10C PstS, T10G PstS, S38F PstS, D56V PstS, D56A PstS, D56L PstS, D56S PstS, S139T PstS, S139P PstS, S139L PstS, and T141H PstS under the transcriptional control of the wild-type *E. coli* pstS gene promoter.

* * * * *

UNITED STATES PATENT AND TRADEMARK OFFICE
CERTIFICATE OF CORRECTION

PATENT NO. : 5,304,472
DATED : 4/19/94
INVENTOR(S) : Steven Bass and James R. Swartz It is certified that error appears in the above-identified that said Letters Patent is hereby corrected as shown below:

In column 49, claim 6, line 38, replace "bacterial" with --Enterobacteriaceae--.
In column 49, claim 7, line 48, insert --6 wherein-- after "claim".
In column 49, claim 11, line 59, replace "exogeneres" with --exogenous--.
In column 50, claim 17, line 32 replace "bacterial" with --Enterobacteriaceae--.
In column 50, claim 17, line 38, replace "bacterial" with --Enterobacteriacea--.
In column 50, claim 20, line 55, replace "clan" with --claim 17--.

Signed and Sealed this

Second Day of May, 1995

*Attest:*

BRUCE LEHMAN

*Attesting Officer*  Commissioner of Patents and Trademarks

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 1400 bases
( B ) TYPE: nucleic acid
( C ) STRANDEDNESS: single
( D ) TOPOLOGY: linear ( x i ) SEQUENCE DESCRIPTION: SEQ ID NO:1:

```
TTCCTGTTAT   GTTTTTAATC   AAACATCCTG   CCAACTCCAT   GTGACAAACC    50

GTCATCTTCG   GCTACTTTTT   CTCTGTCACA   GAATGAAAAT   TTTTCTGTCA   100

TCTCTTCGTT   ATTAATGTTT   GTAATTGACT   GAATATCAAC   GCTTATTTAA   150

ATCAGACTGA   AGACTTTATC   TCTCTGTCAT   AAAACTGTCA   TATTCCTTAC   200

ATATAACTGT   CACCTGTTTG   TCCTATTTTG   CTTCTCGTAG   CCAACAAACA   250
```

```
ATGCTTTATG AATCCTCCCA GGAGACATTA TGAAAGTTAT GCGTACCACC    300
GTCGCAACTG TTGTCGCCGC GACCTTATCG ATGAGTGCTT TCTCTGTGTT    350
TGCAGAAGCA AGCCTGACAG GTGCAGGTGC AACCTTCCCT GCGCCGGTGT    400
ATGCCAAATG GGCTGACACT TACCAGAAAG AAACCGGTAA TAAAGTTAAC    450
TACCAGGGTA TCGGTTCTTC CGGTGGCGTA AAACAGATTA TCGCTAATAC    500
CGTTGATTTT GGTGCCTCTG ACGCGCCGCT GTCTGACGAA AAACTGGCTC    550
AGGAAGGTCT GTTCCAGTTC CCGACCGTGA TTGGCGGCGT GGTGCTGGCG    600
GTTAACATTC CAGGGCTGAA GTCTGGCGAA CTGGTGCTGG ATGGTAAAAC    650
CCTCGGCGAC ATCTACCTGG GCAAAATCAA GAAGTGGGAT GATGAAGCCA    700
TCGCCAAACT GAATCCGGGT CTGAAACTGC CTTCACAAAA CATTGCTGTA    750
GTACGCCGCG CAGATGGCTC CGGGACTTCC TTCGTCTTCA CCAGCTACCT    800
GGCGAAAGTG AACGAAGAGT GGAAAAACAA CGTTGGTACT GGCTCTACCG    850
TAAAATGGCC GATCGGTCTG GGCGGTAAAG GTAACGACGG TATCGCCGCG    900
TTCGTTCAGC GTCTGCCGGG TGCAATTGGT TATGTTGAAT ATGCTTACGC    950
GAAGCAGAAC AACCTGGCGT ACACCAAACT GATCTCCGCT GATGGTAAAC   1000
CGGTTAGTCC GACCGAAGAA AACTTCGCTA ATGCAGCAAA AGGTGCAGAC   1050
TGGAGCAAAA CCTTCGCTCA GGATCTGACC AACCAGAAAG GCGAAGATGC   1100
ATGGCCTATT ACCTCTACCA CGTTCATTCT GATCCACAAA GATCAGAAGA   1150
AACCAGAACA AGGCACAGAA GTGCTGAAAT TCTTCGACTG GGCGTACAAA   1200
ACCGGGGCTA AACAGGCGAA CGACCTGGAT TACGCCAGCC TGCCGGATAG   1250
TGTAGTTGAA CAGGTTCGCG CTGCGTGGAA GACCAATATT AAAGACAGTA   1300
GCGGTAAGCC GCTGTACTAA TAAAACTCCA GGCCGGGTAC GGTGTTTTAC   1350
GCCGCATCCG GCATTACAAA ATGACTTTGT AAACGCGTTT AACTGAAGAG   1400
```

( 2 ) INFORMATION FOR SEQ ID NO:2:

( i ) SEQUENCE CHARACTERISTICS:
        ( A ) LENGTH: 348 amino acids
        ( B ) TYPE: amino acid
        ( D ) TOPOLOGY: linear ( x i ) SEQUENCE DESCRIPTION: SEQ ID NO:2:

```
Met Lys Val Met Arg Thr Thr Val Ala Thr Val Val Ala Ala Thr
 1               5                  10                  15

Leu Ser Met Ser Ala Phe Ser Val Phe Ala Glu Ala Ser Leu Thr
                20                  25                  30

Gly Ala Gly Ala Thr Phe Pro Ala Pro Val Tyr Ala Lys Trp Ala
                35                  40                  45

Asp Thr Tyr Gln Lys Glu Thr Gly Asn Lys Val Asn Tyr Gln Gly
                50                  55                  60

Ile Gly Ser Ser Gly Gly Val Lys Gln Ile Ile Ala Asn Thr Val
                65                  70                  75

Asp Phe Gly Ala Ser Asp Ala Pro Leu Ser Asp Glu Lys Leu Ala
                80                  85                  90

Gln Glu Gly Leu Phe Gln Phe Pro Thr Val Ile Gly Gly Val Val
                95                 100                 105

Leu Ala Val Asn Ile Pro Gly Leu Lys Ser Gly Glu Leu Val Leu
               110                 115                 120

Asp Gly Lys Thr Leu Gly Asp Ile Tyr Leu Gly Lys Ile Lys Lys
```

|     |     |     |     | 125 |     |     |     |     | 130 |     |     |     |     | 135 |
|-----|-----|-----|-----|-----|-----|-----|-----|-----|-----|-----|-----|-----|-----|-----|
| Trp | Asp | Asp | Glu | Ala | Ile | Ala | Lys | Leu | Asn | Pro | Gly | Leu | Lys | Leu |
|     |     |     |     | 140 |     |     |     |     | 145 |     |     |     |     | 150 |
| Pro | Ser | Gln | Asn | Ile | Ala | Val | Val | Arg | Arg | Ala | Asp | Gly | Ser | Gly |
|     |     |     |     | 155 |     |     |     |     | 160 |     |     |     |     | 165 |
| Thr | Ser | Phe | Val | Phe | Thr | Ser | Tyr | Leu | Ala | Lys | Val | Asn | Glu | Glu |
|     |     |     |     | 170 |     |     |     |     | 175 |     |     |     |     | 180 |
| Trp | Lys | Asn | Asn | Val | Gly | Thr | Gly | Ser | Thr | Val | Lys | Trp | Pro | Ile |
|     |     |     |     | 185 |     |     |     |     | 190 |     |     |     |     | 195 |
| Gly | Leu | Gly | Gly | Lys | Gly | Asn | Asp | Gly | Ile | Ala | Ala | Phe | Val | Gln |
|     |     |     |     | 200 |     |     |     |     | 205 |     |     |     |     | 210 |
| Arg | Leu | Pro | Gly | Ala | Ile | Gly | Tyr | Val | Glu | Tyr | Ala | Tyr | Ala | Lys |
|     |     |     |     | 215 |     |     |     |     | 220 |     |     |     |     | 225 |
| Gln | Asn | Asn | Leu | Ala | Tyr | Thr | Lys | Leu | Ile | Ser | Ala | Asp | Gly | Lys |
|     |     |     |     | 230 |     |     |     |     | 235 |     |     |     |     | 240 |
| Pro | Val | Ser | Pro | Thr | Glu | Glu | Asn | Phe | Ala | Asn | Ala | Ala | Lys | Gly |
|     |     |     |     | 245 |     |     |     |     | 250 |     |     |     |     | 255 |
| Ala | Asp | Trp | Ser | Lys | Thr | Phe | Ala | Gln | Asp | Leu | Thr | Asn | Gln | Lys |
|     |     |     |     | 260 |     |     |     |     | 265 |     |     |     |     | 270 |
| Gly | Glu | Asp | Ala | Trp | Pro | Ile | Thr | Ser | Thr | Thr | Phe | Ile | Leu | Ile |
|     |     |     |     | 275 |     |     |     |     | 280 |     |     |     |     | 285 |
| His | Lys | Asp | Gln | Lys | Lys | Pro | Glu | Gln | Gly | Thr | Glu | Val | Leu | Lys |
|     |     |     |     | 290 |     |     |     |     | 295 |     |     |     |     | 300 |
| Phe | Phe | Asp | Trp | Ala | Tyr | Lys | Thr | Gly | Ala | Lys | Gln | Ala | Asn | Asp |
|     |     |     |     | 305 |     |     |     |     | 310 |     |     |     |     | 315 |
| Leu | Asp | Tyr | Ala | Ser | Leu | Pro | Asp | Ser | Val | Val | Glu | Gln | Val | Arg |
|     |     |     |     | 320 |     |     |     |     | 325 |     |     |     |     | 330 |
| Ala | Ala | Trp | Lys | Thr | Asn | Ile | Lys | Asp | Ser | Ser | Gly | Lys | Pro | Leu |
|     |     |     |     | 335 |     |     |     |     | 340 |     |     |     |     | 345 |
| Tyr | Xaa | Xaa |     |     |     |     |     |     |     |     |     |     |     |     |
|     |     | 348 |     |     |     |     |     |     |     |     |     |     |     |     |

( 2 ) INFORMATION FOR SEQ ID NO:3:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGAATTCTGT CATCTCTTCG TTAT 24

( 2 ) INFORMATION FOR SEQ ID NO:4:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

CTGCCCGAGC CATAAGTTAC TCTTCAG 27

( 2 ) INFORMATION FOR SEQ ID NO:5:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

GACAGGTGCA GGCGCCGCCT CCCCTGC 27

( 2 ) INFORMATION FOR SEQ ID NO:6:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

CAGGGTATCG GTGGCTCGGG TGGCGTAA 28

( 2 ) INFORMATION FOR SEQ ID NO:7:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( x i ) SEQUENCE DESCRIPTION: SEQ ID NO:7:

TTTGGTGCCT CTGCAGCGCC GCTGT 25

( 2 ) INFORMATION FOR SEQ ID NO:8:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

GCTGTAGTAC GCGCTGCAGA TGGCT 25

( 2 ) INFORMATION FOR SEQ ID NO:9:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

GTACGCCGCG CTGCAGGCTC CGGGA 25

( 2 ) INFORMATION FOR SEQ ID NO:10:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

CGCAGATGGC GCCGGGACTT C 21

( 2 ) INFORMATION FOR SEQ ID NO:11:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( x i ) SEQUENCE DESCRIPTION: SEQ ID NO:11:

GATGGCTCCG GCGCCTCCTT CGCTT 25

( 2 ) INFORMATION FOR SEQ ID NO:12:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( x i ) SEQUENCE DESCRIPTION: SEQ ID NO:12:

GACAGGTGCA GGCGCCNNST TCCCTGCGCC G 31

( 2 ) INFORMATION FOR SEQ ID NO:13:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( x i ) SEQUENCE DESCRIPTION: SEQ ID NO:13:

CAGGGTATCG GTNNSTCCGG TGGCGTA 27

( 2 ) INFORMATION FOR SEQ ID NO:14:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( x i ) SEQUENCE DESCRIPTION: SEQ ID NO:14:

GTTGATTTTG GCGCCTCTNN SGCGCCGCTG TCT 33

( 2 ) INFORMATION FOR SEQ ID NO:15:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( x i ) SEQUENCE DESCRIPTION: SEQ ID NO:15:

CGCGCAGATG GCNNSGGGAC TTCCT 25

( 2 ) INFORMATION FOR SEQ ID NO:16:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( x i ) SEQUENCE DESCRIPTION: SEQ ID NO:16:

GATGGCTCCG GGNNSTCCTT CGCTT 25

( 2 ) INFORMATION FOR SEQ ID NO:17:

( i ) SEQUENCE CHARACTERISTICS:
        ( A ) LENGTH: 55 bases
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGTCCCGAAA CTCTGTGCGG TGCTGAACTG GTTGACGCTC TGCAGTTTGT 50

TTGCG 55

( 2 ) INFORMATION FOR SEQ ID NO:18:

( i ) SEQUENCE CHARACTERISTICS:
  ( A ) LENGTH: 64 bases
  ( B ) TYPE: nucleic acid
  ( C ) STRANDEDNESS: single
  ( D ) TOPOLOGY: linear ( x i ) SEQUENCE DESCRIPTION: SEQ ID NO:18:

ACGTCCAGGG CTTTGAGACA CGCCACGACT TGACCAACTG CGAGACGTCA 50

AACAAACGCC ACTG 64

( 2 ) INFORMATION FOR SEQ ID NO:19:

( i ) SEQUENCE CHARACTERISTICS:
    ( A ) LENGTH: 84 bases
    ( B ) TYPE: nucleic acid
    ( C ) STRANDEDNESS: single
    ( D ) TOPOLOGY: linear ( x i ) SEQUENCE DESCRIPTION: SEQ ID NO:19:

CTAGAATTAT GATGATTACT CTGCGCAAAC TTCCTCTGGC GGTTGCCGTC 50

GCAGCGGGCG TAATGTCTGC TCAGGCCATG GCCA 84

( 2 ) INFORMATION FOR SEQ ID NO:20:

( i ) SEQUENCE CHARACTERISTICS:
    ( A ) LENGTH: 84 bases
    ( B ) TYPE: nucleic acid
    ( C ) STRANDEDNESS: single
    ( D ) TOPOLOGY: linear ( x i ) SEQUENCE DESCRIPTION: SEQ ID NO:20:

TTAATACTAC TAATGAGACG CGTTTGAAGG AGACCGCCAA CGGCAGCGTC 50

GCCCGCATTA CAGACGAGTC CGGTACCGGT CTAG 84

( 2 ) INFORMATION FOR SEQ ID NO:21:

( i ) SEQUENCE CHARACTERISTICS:
    ( A ) LENGTH: 59 bases
    ( B ) TYPE: nucleic acid
    ( C ) STRANDEDNESS: single
    ( D ) TOPOLOGY: linear ( x i ) SEQUENCE DESCRIPTION: SEQ ID NO:21:

GGCCGGTCCC GAAACTCTGT GCGGTGCTGA ACTGGTTGAC GCTCTGCAGT 50

TTGTTTGCG 59

( 2 ) INFORMATION FOR SEQ ID NO:22:

( i ) SEQUENCE CHARACTERISTICS:
    ( A ) LENGTH: 60 bases
    ( B ) TYPE: nucleic acid
    ( C ) STRANDEDNESS: single
    ( D ) TOPOLOGY: linear ( x i ) SEQUENCE DESCRIPTION: SEQ ID NO:22:

CCAGGGCTTT GAGACACGCC ACGACTTGAC CAACTGCGAG ACGTCAAACA 50

AACGCCACTG 60

( 2 ) INFORMATION FOR SEQ ID NO:23:

( i ) SEQUENCE CHARACTERISTICS:
    ( A ) LENGTH: 50 bases
    ( B ) TYPE: nucleic acid
    ( C ) STRANDEDNESS: single
    ( D ) TOPOLOGY: linear ( x i ) SEQUENCE DESCRIPTION: SEQ ID NO:23:

GGCCACTCTG TGCGGTGCTG AACTGGTTGA CGCTCTGCAG TTTGTTTGCG  50

( 2 ) INFORMATION FOR SEQ ID NO:24:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( x i ) SEQUENCE DESCRIPTION: SEQ ID NO:24:

TGAGACACGC CACGACTTGA CCAACTGCGA GACGTCAAAC AAACGCCACT  50

G  51

( 2 ) INFORMATION FOR SEQ ID NO:25:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( x i ) SEQUENCE DESCRIPTION: SEQ ID NO:25:

CCTAACGCTC GGTTGCCGCC GGGCGTTTTT TATTGTTAA  39

( 2 ) INFORMATION FOR SEQ ID NO:26:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( x i ) SEQUENCE DESCRIPTION: SEQ ID NO:26:

GGATTGCGAG CCAACGGCGG CCCGCAAAAA ATAACAATT  39

( 2 ) INFORMATION FOR SEQ ID NO:27:

( i ) SEQUENCE CHARACTERISTICS:
        ( A ) LENGTH: 757 bases
        ( B ) TYPE: nucleic acid
        ( C ) STRANDEDNESS: single
        ( D ) TOPOLOGY: linear ( x i ) SEQUENCE DESCRIPTION: SEQ ID NO:27:

GAATTCAACT TCTCCATACT TTGGATAAGG AAATACAGAC ATGAAAAATC  50
TCATTGCTGA GTTGTTATTT AAGCTTGCCC AAAAAGAAGA AGAGTCGAAT  100
GAACTGTGTG CGCAGGTAGA AGCTTTGGAG ATTATCGTCA CTGCAATGCT  150
TCGCAATATG GCGCAAAATG ACCAACAGCG GTTGATTGAT CAGGTAGAGG  200
GGGCGCTGTA CGAGGTAAAG CCCGATGCCA GCATTCCTGA CGACGATACG  250
GAGCTGCTGC GCGATTACGT AAAGAAGTTA TTGAAGCATC CTCGTCAGTA  300
AAAGTTAAT CTTTTCAACA GCTGTCATAA AGTTGTCACG GCCGAGACTT  350
ATAGTCGCTT TGTTTTTATT TTTTAATGTA TTTGTAACTA GTACGCAAGT  400
TCACGTAAAA AGGGTATCTA GAATTATGAT GATTACTCTG CGCAAACTTC  450
CTCTGGCGGT TGCCGTCGCA GCGGGCGTAA TGTCTGCTCA GGCCATGGCC  500
GGTCCCGAAA CTCTGTGCGG TGCTGAACTG GTTGACGCTC TGCAGTTTGT  550
TTGCGGTGAC CGTGGTTTTT ATTTAACAA ACCCACTGGT TATGGTTCTT  600
CTTCTCGTCG TGCTCCCCAG ACTGGTATTG TTGACGAATG CTGCTTTCGT  650

```
TCTTGCGACC TGCGTCGTCT GGAAATGTAT TGCGCTCCCC TGAAACCCGC 700

TAAATCTGCT TAGAAGCTCC TAACGCTCGG TTGCCGCCGG GCGTTTTTTA 750

TTGTTAA 757
```

( 2 ) INFORMATION FOR SEQ ID NO:28:

( i ) SEQUENCE CHARACTERISTICS:
        ( A ) LENGTH: 94 amino acids
        ( B ) TYPE: amino acid
        ( D ) TOPOLOGY: linear ( x i ) SEQUENCE DESCRIPTION: SEQ ID NO:28:

```
Met Ile Thr Leu Arg Lys Leu Pro Leu Ala Val Ala Val Ala Ala
 1               5                  10                  15

Gly Val Met Ser Ala Gln Ala Met Ala Gly Pro Glu Thr Leu Cys
                20                  25                  30

Gly Ala Glu Leu Val Asp Ala Leu Gln Phe Val Cys Gly Asp Arg
                35                  40                  45

Gly Phe Tyr Phe Asn Lys Pro Thr Gly Tyr Gly Ser Ser Ser Arg
                50                  55                  60

Arg Ala Pro Gln Thr Gly Ile Val Asp Glu Cys Cys Phe Arg Ser
                65                  70                  75

Cys Asp Leu Arg Arg Leu Glu Met Tyr Cys Ala Pro Leu Lys Pro
                80                  85                  90

Ala Lys Ser Ala
                94
```

( 2 ) INFORMATION FOR SEQ ID NO:29:

( i ) SEQUENCE CHARACTERISTICS:
        ( A ) LENGTH: 485 bases
        ( B ) TYPE: nucleic acid
        ( C ) STRANDEDNESS: single
        ( D ) TOPOLOGY: linear ( x i ) SEQUENCE DESCRIPTION: SEQ ID NO:29:

```
GAATTCATGA GATTTCCTTC AATTTTTACT GCAGTTTTAT TCGCAGCATC  50

CTCCGCATTA GCTGCTCCAG TCAACACTAC AACAGAAGAT GAAACGGCAC 100

AAATTCCGGC TGAAGCTGTC ATCGGTTACT TAGATTTAGA AGGGGATTTC 150

GATGTTGCTG TTTTGCCATT TTCCAACAGC ACAAATAACG GGTTATTGTT 200

TATAAATACT ACTATTGCCA GCATTGCTGC TAAAGAAGAA GGGGTATCTT 250

TGGATAAAAG AGGTCCGGAA ACTCTGTGCG GCGCTGAGCT GGTTGACGCT 300

CTGCAGTTCG TATGTGGTGA TCGAGGCTTC TACTTCAACA AACCGACTGG 350

GTACGGATCC TCCTCTCGTC GTGCTCCGCA AACCGGCATC GTTGATGAAT 400

GCTGTTTTCG GTCCTGTGAC CTTCGCCGTC TGGAAATGTA CTGCGCTCCG 450

CTGAAACCGG CTAAGTCTGC ATAGTCGACG AATTC 485
```

( 2 ) INFORMATION FOR SEQ ID NO:30:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
CATGGCCGGT CCGGAAACTC TGTGCGGCGC 30
```

(2) INFORMATION FOR SEQ ID NO:31:

(i) SEQUENCE CHARACTERISTICS:
(A) LENGTH: 22 bases
(B) TYPE: nucleic acid
(C) STRANDEDNESS: single
(D) TOPOLOGY: linear (xi) SEQUENCE DESCRIPTION: SEQ ID NO:31:

CGGCCAGGCC TTTGAGACAC GC  22